United States Patent
Czaplewski et al.

(10) Patent No.: US 10,301,435 B2
(45) Date of Patent: *May 28, 2019

(54) FUNCTIONALIZED FLAME-RETARDANT ACONITIC ACID-DERIVED MOLECULES

(71) Applicant: International Business Machines Corporation, Armonk, NY (US)

(72) Inventors: Sarah K. Czaplewski, Rochester, MN (US); Brandon M. Kobilka, Tucson, AZ (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/611,313

(22) Filed: Jun. 1, 2017

(65) Prior Publication Data
US 2018/0346656 A1 Dec. 6, 2018

(51) Int. Cl.
*C08K 5/521* (2006.01)
*C08K 5/524* (2006.01)
(Continued)

(52) U.S. Cl.
CPC ......... *C08G 81/027* (2013.01); *C08G 18/836* (2013.01); *C09J 9/00* (2013.01);
(Continued)

(58) Field of Classification Search
None
See application file for complete search history.

(56) References Cited

U.S. PATENT DOCUMENTS 2,754,319 A * 7/1956 Johnston ............... C07F 9/4006
106/18.14
2016/0251485 A1 9/2016 Boday et al.

FOREIGN PATENT DOCUMENTS

| CN | 103965245 A | 8/2014 | |
| CN | 104356361 A | 2/2015 | |
| GB | 1482784 A * | 8/1977 | ........... H05K 3/0094 |

OTHER PUBLICATIONS

Kian Resin Chemical Co., Data sheet for Poly Star UM 55, retrieved from kianresin.com on Sep. 4, 2018. (Year: 2018).*

(Continued)

*Primary Examiner* — Richard A Huhn
(74) *Attorney, Agent, or Firm* — Kelsey M. Skodje

(57) ABSTRACT

A functionalized flame-retardant aconitic acid-derived molecule, a process for forming a flame-retardant polymer, and an article of manufacture comprising a material that contains a functionalized flame-retardant aconitic acid-derived molecule are disclosed. The functionalized flame-retardant aconitic acid-derived molecule can have at least one phosphoryl or phosphonyl moiety with allyl functional groups, epoxy functional groups, propylene carbonate functional groups, or functionalized thioether substituents. The process for forming the flame-retardant polymer can include reacting an aconitic acid derivative with a flame-retardant phosphorus-based molecule to form a functionalized flame-retardant aconitic acid-derived molecule, and combining the functionalized flame-retardant aconitic acid-derived molecule with a polymer. The material in the article of manufacture can be a resin, plastic, polymer, or adhesive, and the article of manufacture can further comprise an electronic component.

17 Claims, 21 Drawing Sheets

(51) Int. Cl.
    C07F 9/02      (2006.01)
    C08G 81/02     (2006.01)
    C08G 18/83     (2006.01)
    C09J 9/00      (2006.01)
    C09J 175/04    (2006.01)
    C09J 187/00    (2006.01)
    H05K 1/03      (2006.01)
    C07C 69/003    (2006.01)
    C07F 9/09      (2006.01)
    C07F 9/141     (2006.01)
    C07F 9/113     (2006.01)
    C07C 69/007    (2006.01)
    C08K 5/00      (2006.01)

(52) U.S. Cl.
    CPC ......... *C09J 175/04* (2013.01); *C09J 187/005* (2013.01); *H05K 1/032* (2013.01); *C07C 69/003* (2013.01); *C07C 69/007* (2013.01); *C07F 9/091* (2013.01); *C07F 9/093* (2013.01); *C07F 9/113* (2013.01); *C07F 9/1411* (2013.01); *C07F 9/1412* (2013.01); *C08K 5/0066* (2013.01); *C08K 5/521* (2013.01); *C08K 5/524* (2013.01); *C08L 2201/02* (2013.01); *C08L 2666/84* (2013.01); *C09J 2203/326* (2013.01); *C09J 2453/00* (2013.01); *C09J 2475/00* (2013.01)

(56) References Cited

OTHER PUBLICATIONS

Mengal et al., "Citric acid based durable and sustainable flame retardant treatment for lyocell fabric," Carbohydrate Polymers, vol. 153, 2016, pp. 78-88, Elsevier. DOI: 10.1016/j.carbpol.2016.07.074.

Czaplewski et al., "Flame-Retardant Aconitic Acid-Derived Small Molecules," U.S. Appl. No. 15/611,237, filed Jun. 1, 2017.

Czaplewski et al., "Flame-Retardant Aconitic Acid-Derived Cross-Linkers," U.S. Appl. No. 15/611,360, filed Jun. 1, 2017.

Czaplewski et al., "Flame-Retardant Aconitic Acid-Derived Monomers" U.S. Appl. No. 15/611,423, filed Jun. 1, 2017.

List of IBM Patents or Patent Applications Treated as Related, Signed Jun. 1, 2017, 2 pages.

Meyer et al., "The synthesis of citric acid phosphate," Journal of the American Chemical Society, 1959, 81, pp. 2094-2096 (Abstract Only).

* cited by examiner

2-Mercaptoethanol 335

Cysteamine HCl 340

3-Mercaptopropionate 345

302

PG = TMS, TES, TPS, TIPS, MOM, THP

FUNCTIONALIZED FLAME-RETARDANT ACONITIC ACID-DERIVED MOLECULES

BACKGROUND

The present disclosure relates to bio-renewable flame-retardant compounds and, more specifically, polymer-bondable functionalized flame-retardant molecules derived from aconitic acid.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Aconitic acid (propene-1,2,3-tricarboxylic acid) is one example of a bio-based compound that can have applications as a component of various polymers, resins, and small molecules. Aconitic acid is an intermediate in the citric acid cycle, wherein it is acted upon by the aconitase enzyme. Bio-based materials, such as sugarcane or citric acid, are common sources of aconitic acid.

SUMMARY

Various embodiments are directed to functionalized flame-retardant aconitic acid-derived molecules. The functionalized flame-retardant aconitic acid-derived molecules can have at least one phosphoryl or phosphonyl moiety, as well as an allyl functional group, epoxy functional group, propylene carbonate functional group, or functionalized thioether substituent. The functionalized thioether substituent can be a hydroxyl-functionalized thioether substituent, an amino-functionalized thioether substituent, or a carboxylic acid-functionalized thioether substituent. Additional embodiments are directed to forming a flame-retardant polymer. The polymer can be produced by forming an aconitic acid derivative, forming a phosphorus-based flame-retardant molecule, and reacting the aconitic acid derivative and the phosphorus-based flame-retardant molecule to form a functionalized flame-retardant aconitic acid-derived molecule. The functionalized flame-retardant aconitic acid-derived molecule can be further reacted with thiol molecules or a combination of lithium bromide and carbon dioxide to form functionalized flame-retardant aconitic acid-derived molecules with functionalized thioether substituents or propylene carbonate functional groups, respectively. The functionalized flame-retardant aconitic acid-derived molecule can then be bound to a polymer, forming the flame-retardant polymer. The aconitic acid derivatives can be phenol functionalized, and synthesized from aconitic acid that has been obtained from a bio-based source. The phosphorus-based flame-retardant molecule can be a phosphate-based molecule or a phosphonate-based molecule with at least one allyl or epoxy functional group. Further embodiments are directed to an article of manufacture comprising a material that contains a functionalized flame-retardant aconitic acid-derived molecule. The material can be a resin, plastic, adhesive, or polymer. Examples of polymer materials can include polyurethane, epoxies, polyhydroxyurethane, polycarbonates, polyester, polyacrylates, polyimides, polyamides, polyureas, and poly(vinyl-ester). The article of manufacture can further comprise an electronic component.

DETAILED DESCRIPTION

Bio-based compounds are increasingly being used in the synthesis of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale.

Examples of strategies for producing bio-based compounds can be found in fermentation technologies, membrane technologies, and genetic engineering. Two approaches that can use these technologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of substances that can be produced from bio-based compounds can include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can also impart flame-retardant properties to bio- and petroleum-based polymers. For example, flame-retardant cross-linkers can be incorporated into polymers, and flame-retardant monomers can be polymerized to form flame-retardant polymers. Additionally, flame-retardant molecules can be blended or chemically reacted with the polymers.

Aconitic acid (propene-1,2,3-tricarboxylic acid) is one example of a bio-based compound that can have applications as a component of various polymers, resins, and molecules. Aconitic acid is an intermediate in the conversion of citrate to isocitrate during the citric acid cycle. On an industrial scale, aconitic acid is commonly obtained from fermented sugarcane extract, or synthesized from citric acid. It can be obtained from the plant- and microorganism-based bio-sources discussed above, or synthesized from petroleum-based raw materials. According to some embodiments of the present disclosure, aconitic acid is used as a precursor for flame-retardant molecules. The functionalized flame-retardant aconitic acid-derived molecules can be bound to resins and polymers by their function group, causing the resins and polymers to be flame-retardant.

Figure 1:
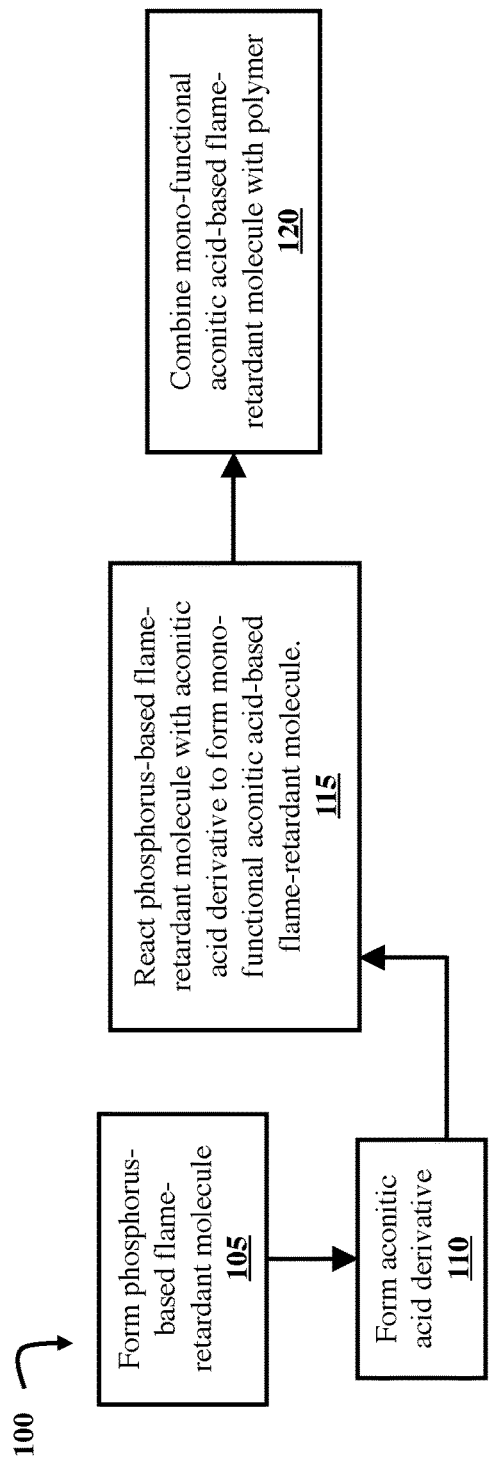
FIG. 1 is a flow diagram illustrating a process of forming a flame-retardant polymer containing a functionalized flame-retardant aconitic acid-derived molecule, according to some embodiments of the present disclosure.

FIG. 1 is a flow diagram illustrating a process 100 of forming a flame-retardant polymer containing a functionalized flame-retardant aconitic acid-derived molecule, according to some embodiments of the present disclosure. Process 100 begins with the formation of a phosphorus-based flame-retardant molecule. This is illustrated at step 105. The phosphorus-based flame-retardant molecule has either a phosphoryl or a phosphonyl moiety (collectively referred to as an FR group) with an attached R group or phenyl (Ph) group. The R groups that are attached to the FR group can vary, as is discussed in greater detail below. The syntheses and structures of phosphorus-based flame-retardant molecules are discussed in greater detail with regard to FIGS. 2, 3A, and 3B.

Process 100 continues with the formation of a phenol-functionalized aconitic acid derivative. This is illustrated at step 110. The syntheses and structures of phenol-functionalized aconitic derivatives are discussed in greater detail with regard to FIGS. 4A-4D. The phenol-functionalized aconitic acid derivative and the phosphorus-based flame-retardant molecule are chemically reacted in order to form a functionalized flame-retardant aconitic acid-derived molecule. This is illustrated at step 115. The structures and syntheses of functionalized flame-retardant aconitic acid-derived molecules are discussed in greater detail with regard to FIGS. 5A-5L.

The identity of the functionalized flame-retardant aconitic acid-derived molecule formed in step 115 is determined by the phenol-functionalized aconitic acid derivative and the phosphorus-based flame-retardant molecule used in the reaction. The phosphorus-based flame-retardant molecule reacts with a hydroxyl group on the phenol-functionalized aconitic acid derivative to provide an FR group with an attached R functional group. Examples of R groups can include phenyl substituents, epoxy functional groups, allyl functional groups, propylene carbonate substituents, hydroxyl-functionalized thioether substituents, amino-functionalized thioether substituents, carboxylic acid-functionalized thioether substituents, etc. The syntheses and structures of the functionalized flame-retardant aconitic acid-derived molecules are discussed in greater detail with regard to FIGS. 5A-5L.

The functionalized flame-retardant aconitic acid-derived molecule formed in step 115 is chemically reacted with a polymer, forming a bond between the flame-retardant functionalized aconitic acid derivatives and the polymer. This is illustrated at step 120. Examples of polymers can include epoxies, polyhydroxyurethanes, polycarbonates, polyesters, polyacrylates, polyimides, polyamides, polyureas, poly(vinyl-esters), etc. The materials for these polymers can come from petroleum-based sources, bio-based sources, or a combination of petroleum- and bio-based sources. Further, in some embodiments, the flame-retardant aconitic acid derivatives can be used in non-polymeric applications, such as resins for varnishes and adhesives.

Figure 2:
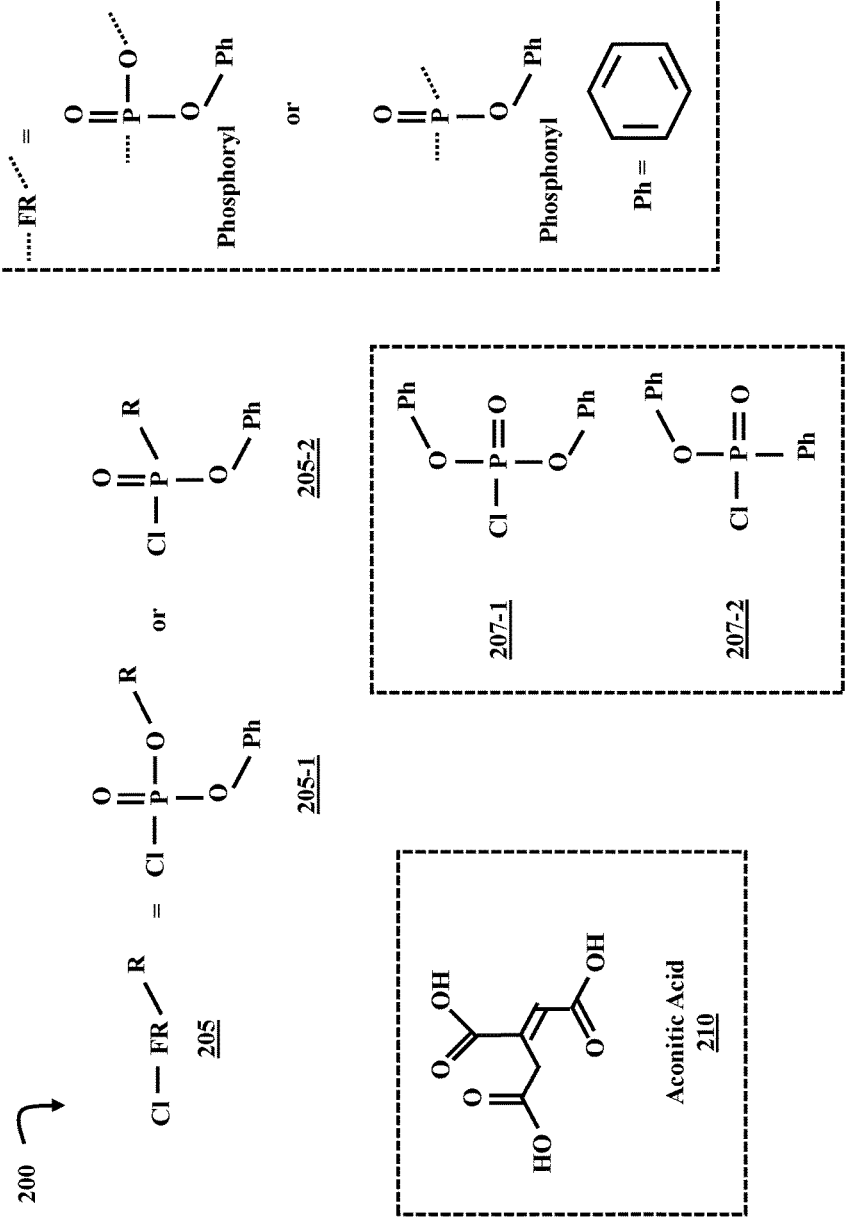
FIG. 2 is a diagrammatic representation of the molecular structures of R-functionalized phosphorus-based flame-retardant molecules, phenyl-substituted flame retardant phosphorus-based flame-retardant molecules, and aconitic acid, according to some embodiments of the present disclosure.

FIG. 2 is a diagrammatic representation of the molecular structures 200 of R-functionalized phosphorus-based flame-retardant molecules 205-1 and 205-2 (referred to collectively as 205), phenyl-substituted flame retardant phosphorus-based flame-retardant 207-1 and 207-2 (referred to collectively as 207), and aconitic acid 210, according to some embodiments of the present disclosure. Each phosphorus-based flame-retardant molecule is either a phosphate-based flame-retardant molecule 205-1 and 207-1 or phosphonate-based flame-retardant molecule 205-2 and 207-2. Herein, phosphoryl and phosphonyl moieties are replaced by the abbreviation "FR" in order to simplify illustrations of the molecular structures.

The phenyl-substituted flame-retardant phosphorus-based flame-retardant molecules 207 each have two phenyl (Ph) substituents. Each R-functionalized phosphorus-based flame-retardant molecule 205 has a phenyl substituent in addition to its R functional group. In some embodiments, one or more phenyl groups on a phosphorus-based flame-retardant molecule are replaced by another alkyl substituent (e.g., ethyl, methyl, propyl, isopropyl, etc.). Prophetic syntheses of the R-functionalized phosphorus-based flame-retardant molecules 205 are discussed with regard to FIGS. 3A and 3B. The phosphorus-based flame-retardant molecules 205 and 207 are reacted with the aconitic acid derivatives to form functionalized flame-retardant aconitic acid-derived molecules. These reactions are discussed in greater detail with regard to FIGS. 4C and 4D, 5A, 5D, 5G, and 5J.

Figure 3A:
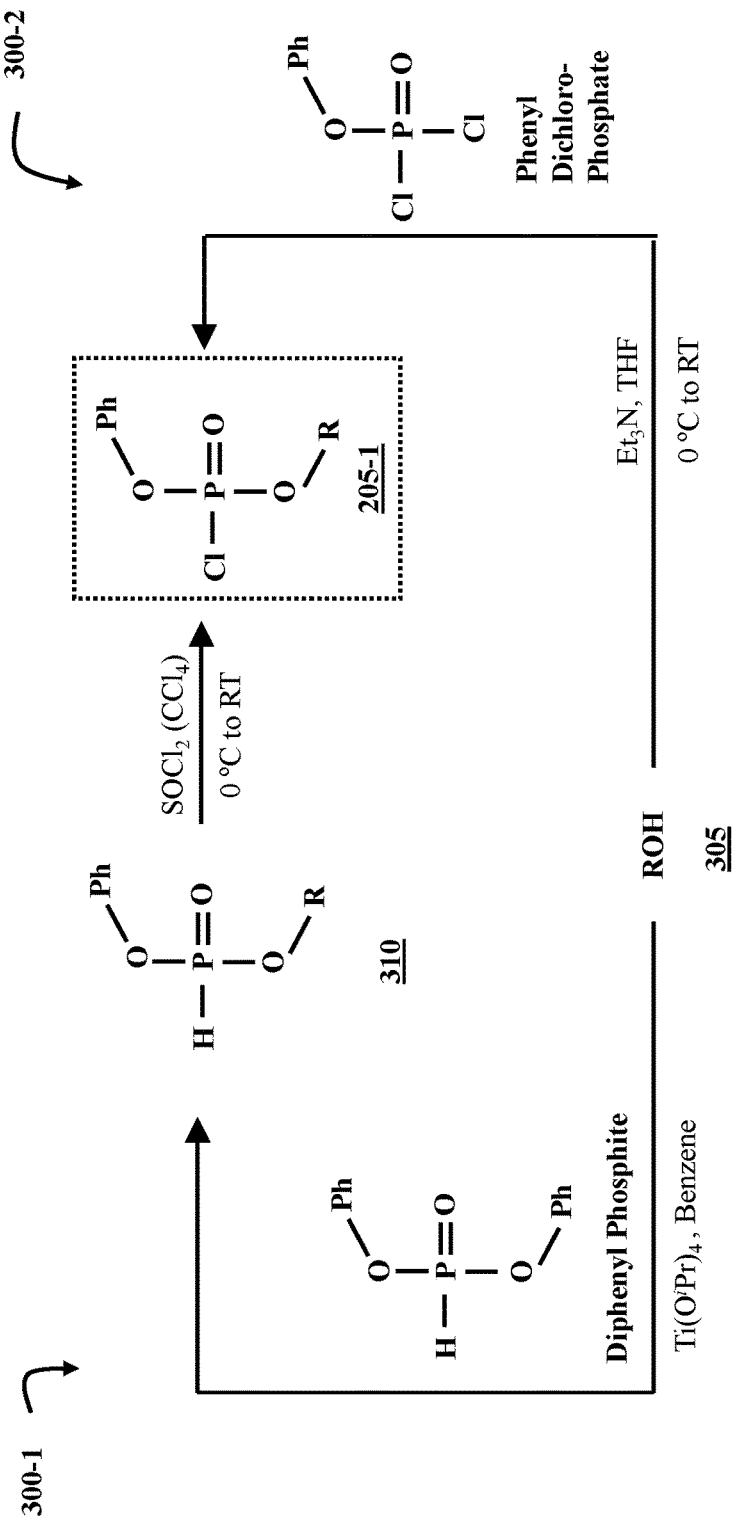
FIG. 3A is a chemical reaction diagram illustrating two processes of synthesizing an R-functionalized phosphate-based flame-retardant molecule, according to some embodiments of the present disclosure.

FIG. 3A is a chemical reaction diagram illustrating two processes 300-1 and 300-2 of synthesizing the R-functionalized phosphate-based flame-retardant molecule 205-1, according to some embodiments of the present disclosure. In both processes 300-1 and 300-2, an alcohol 305 is a starting material for the phosphate-based flame-retardant molecule 205-1. The alcohol 305 has either an allyl R group 307 or an epoxy R group 308. It should be noted that, though an allyl group 307 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphonate and titanium isopropoxide (Ti(O$^i$(Pr)$_4$) in benzene to produce a precursor 310 to the phosphate-based flame-retardant molecule 205-1. In this pseudo-transesterification reaction, the precursor 310 is formed when a phenyl (Ph) substituent on diphenyl phosphite is replaced by the R group from the alcohol 305. The precursor 310 is then reacted with thionyl chloride (SOCl$_2$) and carbon tetrachloride (CCl$_4$) over a range of 0° C. to room temperature (RT, e.g., 15-25° C.), forming the phosphate-based flame-retardant molecule 205-1. In process 300-2, the alcohol 305 is reacted with phenyl dichlorophosphate in a tetrahydrofuran (THF) solution containing triethyl amine (Et$_3$N). This process is carried out over a range of 0° C. to room temperature (RT, e.g., 15-25° C.). A chloride on the phenyl dichlorophosphate is replaced by the alcohol 305, forming the R-functionalized phosphate-based flame-retardant molecule 205-1.

Figure 3B:
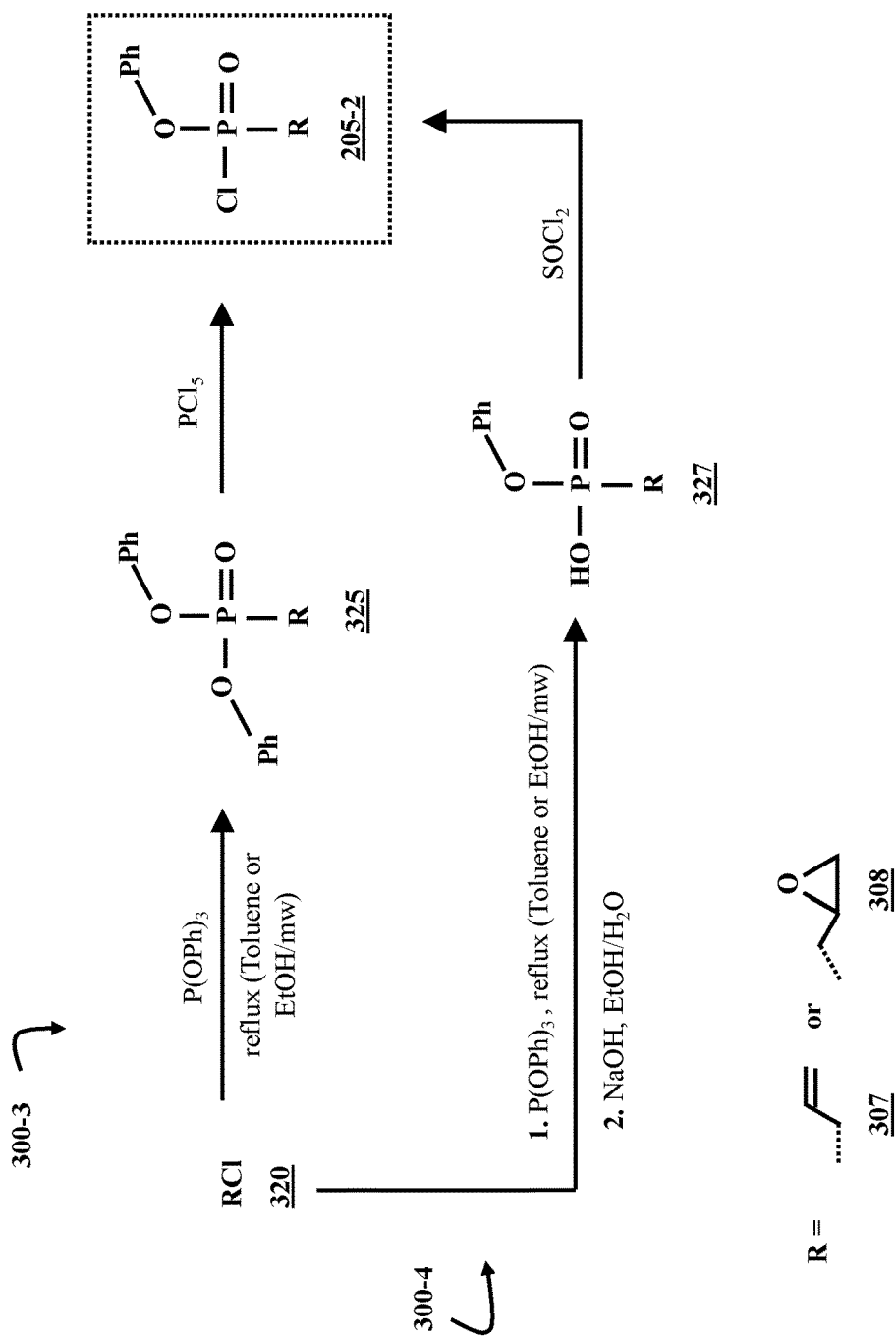
FIG. 3B is a chemical reaction diagram illustrating two processes of synthesizing an R-functionalized phosphonate-based flame-retardant molecule, according to some embodiments of the present disclosure.

FIG. 3B is a chemical reaction diagram illustrating two processes 300-3 and 300-4 of synthesizing the R-functionalized phosphonate-based flame-retardant molecule 205-2, according to some embodiments of the present disclosure. In both processes 300-3 and 300-4, an organochloride 320 is a starting material for the R-functionalized phosphonate-based flame-retardant molecule 205-2. The organochloride has either an allyl R group 307 or an epoxy R group 308. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite (P(OPh)$_3$). The mixture is heated, either by refluxing in toluene or microwaving (mw) in ethanol (EtOH), producing a phosphonyl ester precursor 325 to the R-functionalized phosphonate-based flame-retardant molecule 205-2. The phosphonyl ester precursor 325 is reacted with phosphorus pentachloride (PCl$_5$) to form the R-functionalized phosphonate-based flame-retardant molecule 205-2.

In process 300-4, a mixture of the organochloride 320 and triphenyl phosphite (P(OPh)$_3$) is heated, either by refluxing in toluene or microwaving (mw) in ethanol (EtOH), forming a phenylphosphinic acid precursor 327 to the R-functionalized phosphonate-based flame-retardant molecule 205-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the R-functionalized phosphonate-based flame-retardant molecule 205-2.

Figure 3C:
FIG. 3C is a diagrammatic representation of the molecular structures of three thiol molecules that are involved in the synthesis of functionalized flame-retardant aconitic acid-derived molecules, according to some embodiments of the present disclosure.
Figure 3C:
Figure 3C:
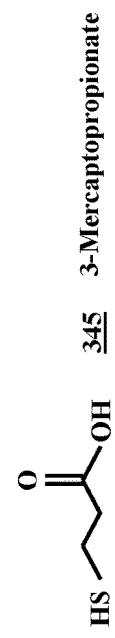

FIG. 3C is a diagrammatic representation of the molecular structures 302 of three thiol molecules that are involved in the synthesis of the functionalized flame-retardant aconitic acid-derived molecules, according to some embodiments of the present disclosure. The three thiol molecules are 2-mercaptoethanol 335, cysteamine hydrochloride (HCl) 340, and 3-mercaptopropionate 345. Each of these thiols can provide a thioether R group in the synthesis of a thioether-linked flame-retardant aconitic acid-derived cross-linker. Details of the syntheses and structures of the thioether-linked flame-retardant aconitic acid derivatives are discussed in greater detail with regard to FIGS. 5B, 5E, 5H, and 5K.

Figure 4A:
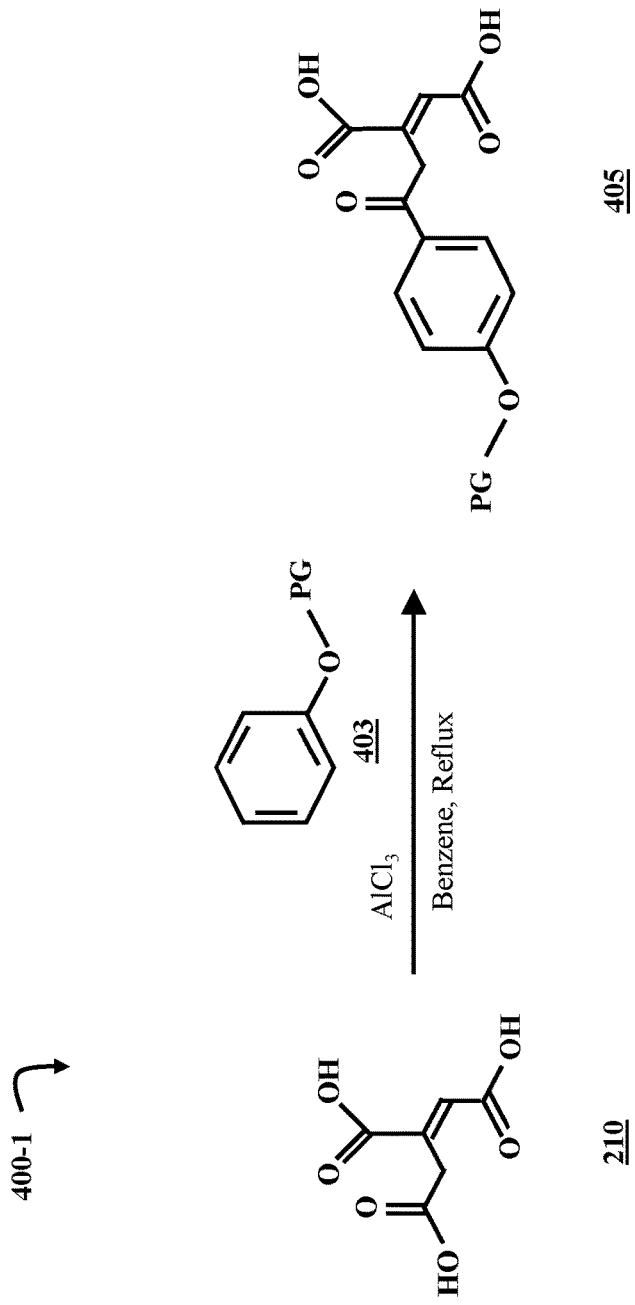
FIG. 4A is a chemical reaction diagram illustrating a process of synthesizing a protected phenol-substituted aconitic acid derivative, according to some embodiments of the present disclosure.

FIG. 4A is a chemical reaction diagram illustrating a process 400-1 of synthesizing a protected phenol-substituted aconitic acid derivative 405, according to some embodiments of the present disclosure. Process 400-1 is a Friedel-Crafts acylation reaction targeting the carboxylic acid moiety bonded to the aliphatic portion of the aconitic acid 210 molecule. In this prophetic example, aconitic acid 210 is combined with a protected phenol (PG-phenol) 403 and aluminum chloride (AlCl$_3$) in a benzene solution. The reaction mixture is refluxed, producing the PG-phenol-substituted aconitic acid derivative 405. The protecting group (PG) on the PG-phenol 403 can vary. Examples of protecting groups can include trimethylsilyl (TMS), triethylsilyl (TES), tert-butyldiphenylsilyl (TBS), triisopropylsilyl (TIPS), methoxymethyl ether (MOM), and tetrahydropyranyl (THP) groups.

Figure 4B:
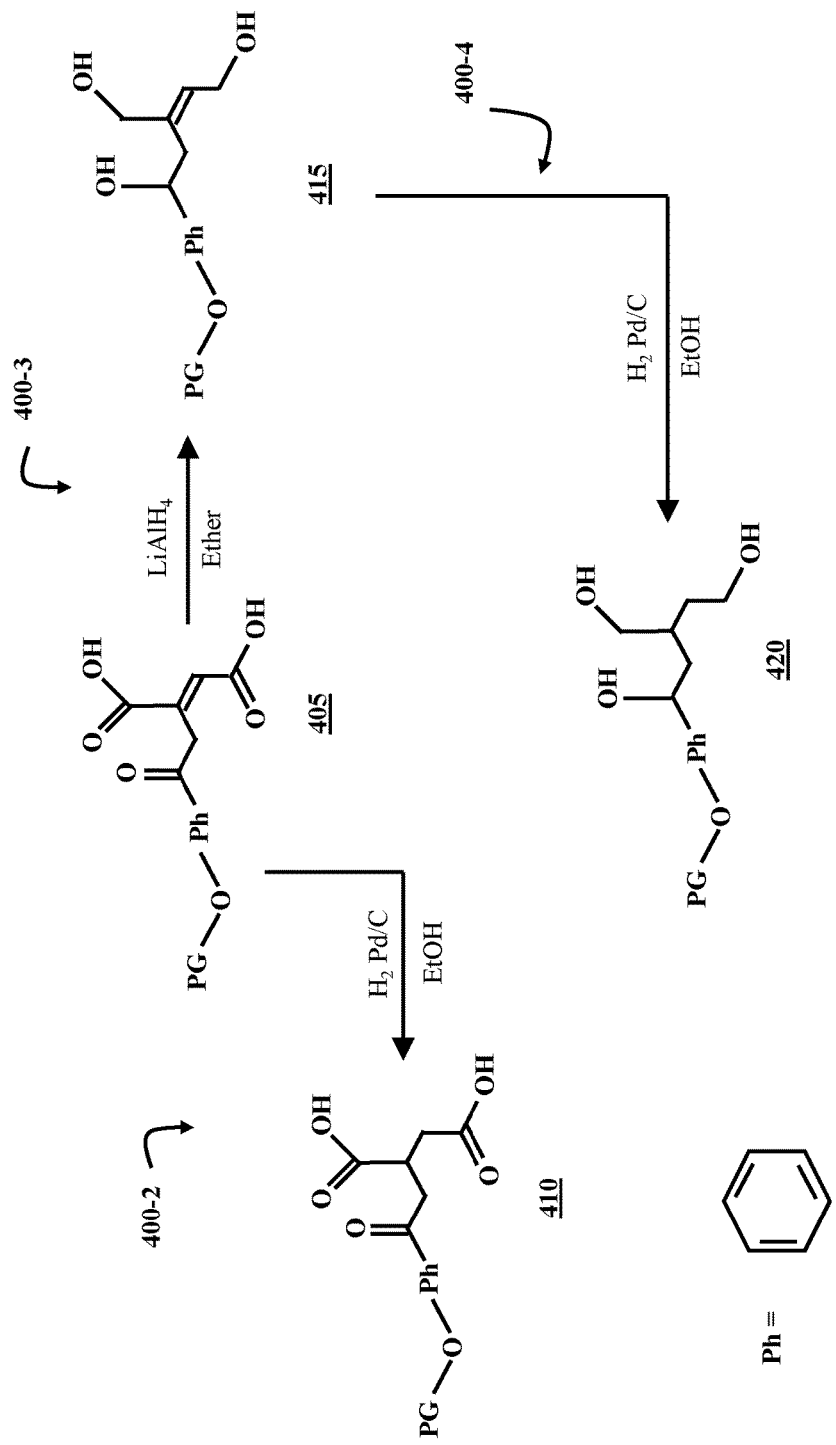
FIG. 4B is a chemical reaction diagram illustrating processes of forming derivatives of the protected phenol-substituted aconitic acid derivative, according to some embodiments of the present disclosure.

FIG. 4B is a chemical reaction diagram illustrating processes 400-2, 400-3, and 400-4 of forming derivatives of the PG-phenol-substituted aconitic acid derivative 405, according to some embodiments of the present disclosure. The derivatives are a PG-phenol-substituted carboxysuccinic acid derivative 410, a PG-phenol-substituted butenetriol derivative 415, and a PG-phenol-substituted butanetriol derivative 420, according to some embodiments of the present disclosure. Each of these processes is a reduction reaction. Though processes 400-2, 400-3, and 400-4 are illustrated as involving the reducing agents LiAlH$_4$ and H$_2$ with Pd/C, in some embodiments, other reducing agents are used (e.g., sodium borohydride ($NaBH_4$), carbon monoxide (CO), iron(II) compounds, etc.).

In process 400-2, the PG-phenol-substituted aconitic acid derivative 405 is reacted with hydrogen ($H_2$) in an ethanol solution. The reaction is catalyzed by palladium on carbon (Pd/C), and produces the PG-phenol-substituted carboxysuccinic acid derivative 410. In process 400-3, the PG-phenol-substituted aconitic acid derivative 405 is reacted with lithium aluminum hydride ($LiAlH_4$) in an ether solution, producing the PG-phenol-substituted butenetriol derivative 415. In process 400-4, the PG-phenol-substituted butenetriol derivative 415 is reacted with hydrogen ($H_2$) in an ethanol (EtOH) solution. The reaction is catalyzed by a palladium on carbon (Pd/C) catalyst, and produces the PG-phenol-substituted butanetriol derivative 420.

Figure 4C:
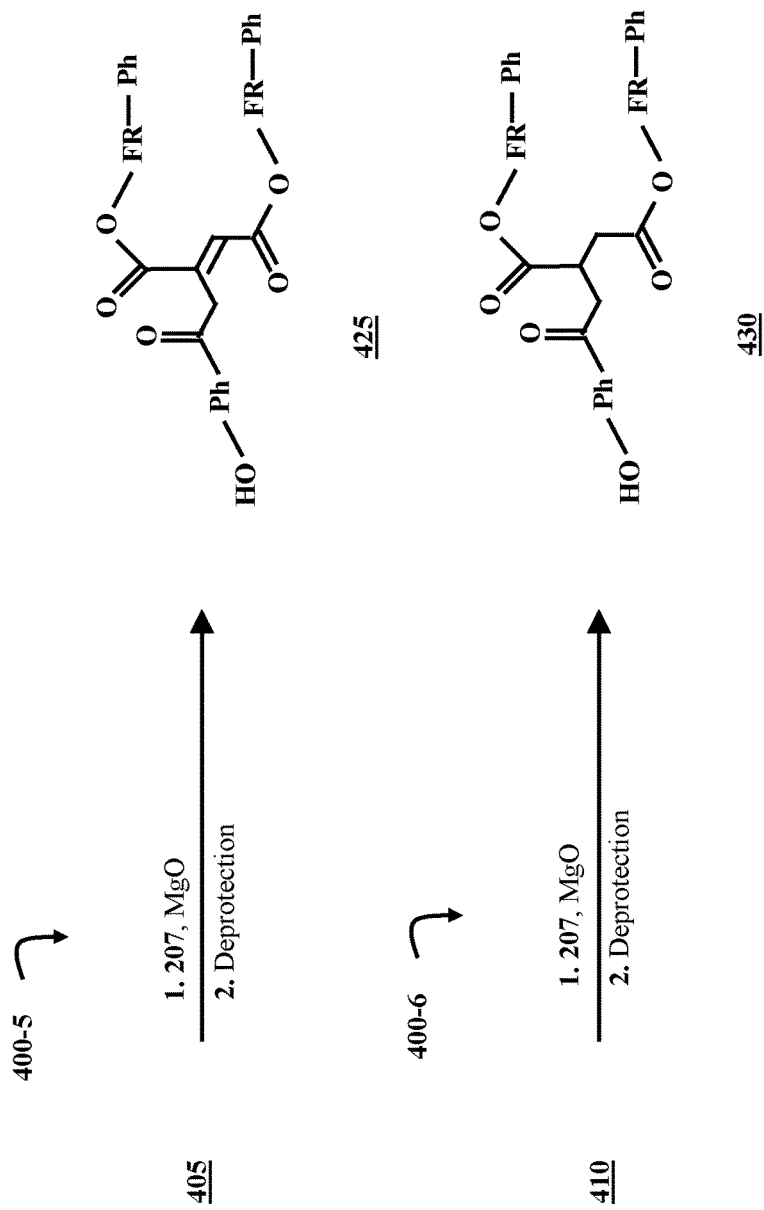
FIG. 4C is a chemical reaction diagram illustrating processes of forming a phenol-functionalized aconitic acid derivative and a carboxysuccinic acid derivative, according to some embodiments of the present disclosure.

FIG. 4C is a chemical reaction diagram illustrating processes 400-5 and 400-6 of forming a phenol-functionalized aconitic acid derivative 425 and a carboxysuccinic acid derivative 430, according to some embodiments of the present disclosure. Each process involves a reaction with a phenyl-substituted phosphorus-based flame-retardant molecule 207, followed by a deprotection reaction. In process 400-5, the PG-phenol-substituted aconitic acid derivative 405 is converted to a phenol-functionalized aconitic acid derivative 425. In process 400-6, the PG-phenol-substituted carboxysuccinic acid derivative 410 is converted to a phenol-functionalized carboxysuccinic acid derivative 430. Processes 400-5 and 400-6 are carried out under substantially the same reaction conditions.

In the first step of processes 400-5 and 400-6, the PG-phenol-substituted aconitic acid derivative 405 is reacted with the phenyl-substituted phosphorus-based flame-retardant molecule 207 in the presence of magnesium oxide (MgO). This reaction binds phenyl (Ph)-substituted flame-retardant (FR) moieties to the hydroxyl groups on the PG-phenol-substituted derivatives 405 or 410. If processes 400-5 and 400-6 are carried out with the phenyl-substituted phosphate-based flame-retardant molecule 207-1, the phenol-functionalized derivatives 425 and 430 will have phosphoryl FR groups, and if the processes 400-5 and 400-6 are carried out with the phenyl-substituted phosphonate-based flame-retardant molecule 207-2, the phenol-functionalized derivatives 425 and 430 will have phosphonyl FR groups.

The second step in processes 400-5 and 400-6 is a deprotection reaction. In this step, the protecting group (PG) is removed. The reaction conditions under which the PG is removed can vary. For example, silyl PGs (e.g., TMS, TES, TBS, and TIPS) can be removed by a reaction with fluorides, such as tetrabutylammonium fluoride (TMF). The silyl PGs, as well as other PGs (e.g., MOM and THP) can also be removed by acids and bases. The deprotection reactions yield the phenol-functionalized aconitic acid derivative 425 and the phenol-functionalized carboxysuccinic acid derivative 430.

Figure 4D:
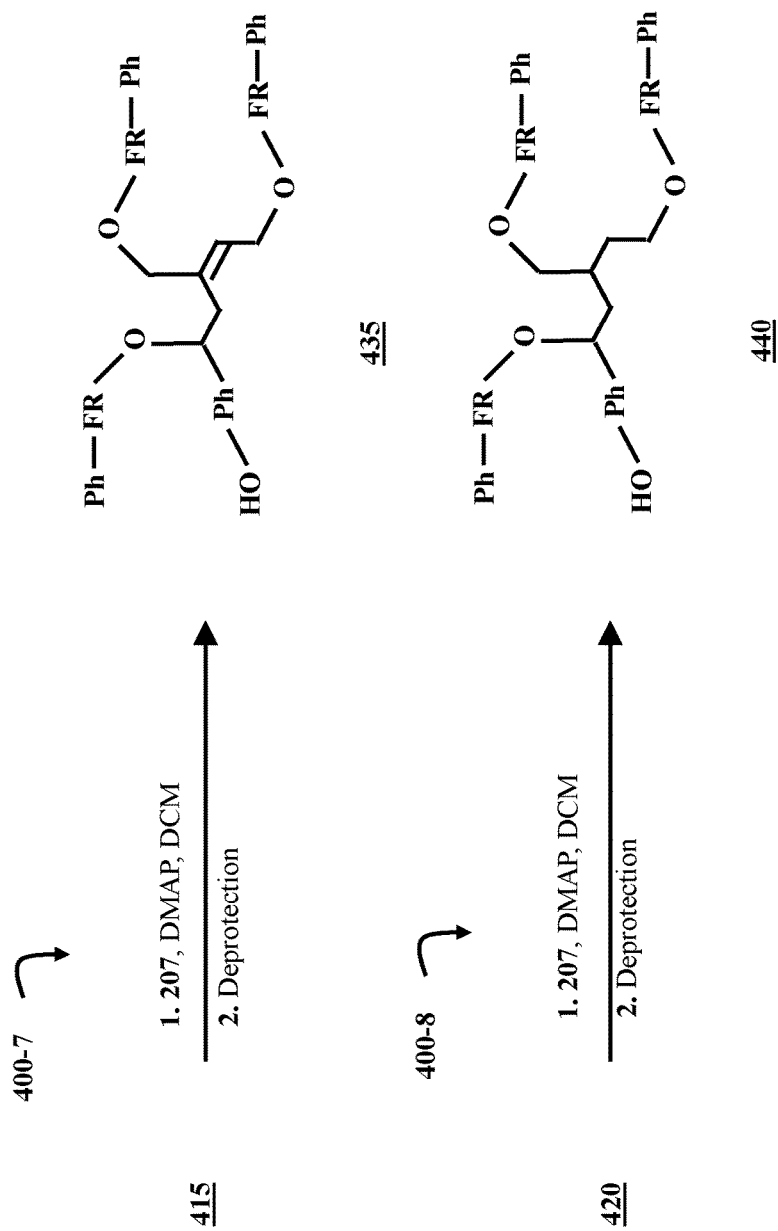
FIG. 4D is a chemical reaction diagram illustrating processes of forming a phenol-functionalized butenetriol derivative and a phenol-functionalized butanetriol derivative, according to some embodiments of the present disclosure.

FIG. 4D is a chemical reaction diagram illustrating processes 400-7 and 400-8 of forming a phenol-functionalized butenetriol derivative 435 and a phenol-functionalized butanetriol derivative 440, according to some embodiments of the present disclosure. Each process involves a reaction with a phenyl-substituted phosphorus-based flame-retardant molecule 207, followed by a deprotection reaction. In process 400-7, the PG-phenol-substituted butenetriol derivative 415 is converted to a phenol-functionalized butenetriol derivative 435. In process 400-8, the PG-phenol-substituted butanetriol derivative 420 is converted to a phenol-functionalized butanetriol derivative 440. Processes 400-7 and 400-8 are carried out under substantially the same reaction conditions as processes 400-5 and 400-6, respectively. Processes 400-5 and 400-6 are described in greater detail with regard to FIG. 4C.

In some embodiments, processes 400-5-400-8 are carried out with a mixture of phenyl-substituted phosphoryl- and phosphonyl-based flame-retardant molecules 207-1 and 207-2. Carrying out processes 400-5-400-8 with a mixture of both phenyl-substituted phosphorus-based molecules 207-1 and 207-2 can result in substituted flame-retardant molecules with both phosphoryl- and phosphonyl FR groups. However, in some instances, adding a mixture of both phenyl-substituted phosphorus-based molecules 207-1 and 207-2 can result in the production of phenol-functionalized flame-retardant molecules with all phosphoryl or all phosphonyl FR groups. Additionally, adding both phenyl-substituted phosphorus-based molecules 207-1 and 207-2 to the reaction can yield a mixture of products that includes some combination of derivatives with either all phosphoryl or all phosphonyl FR groups and derivatives with both phosphoryl and phosphonyl FR groups.

Figure 5A:
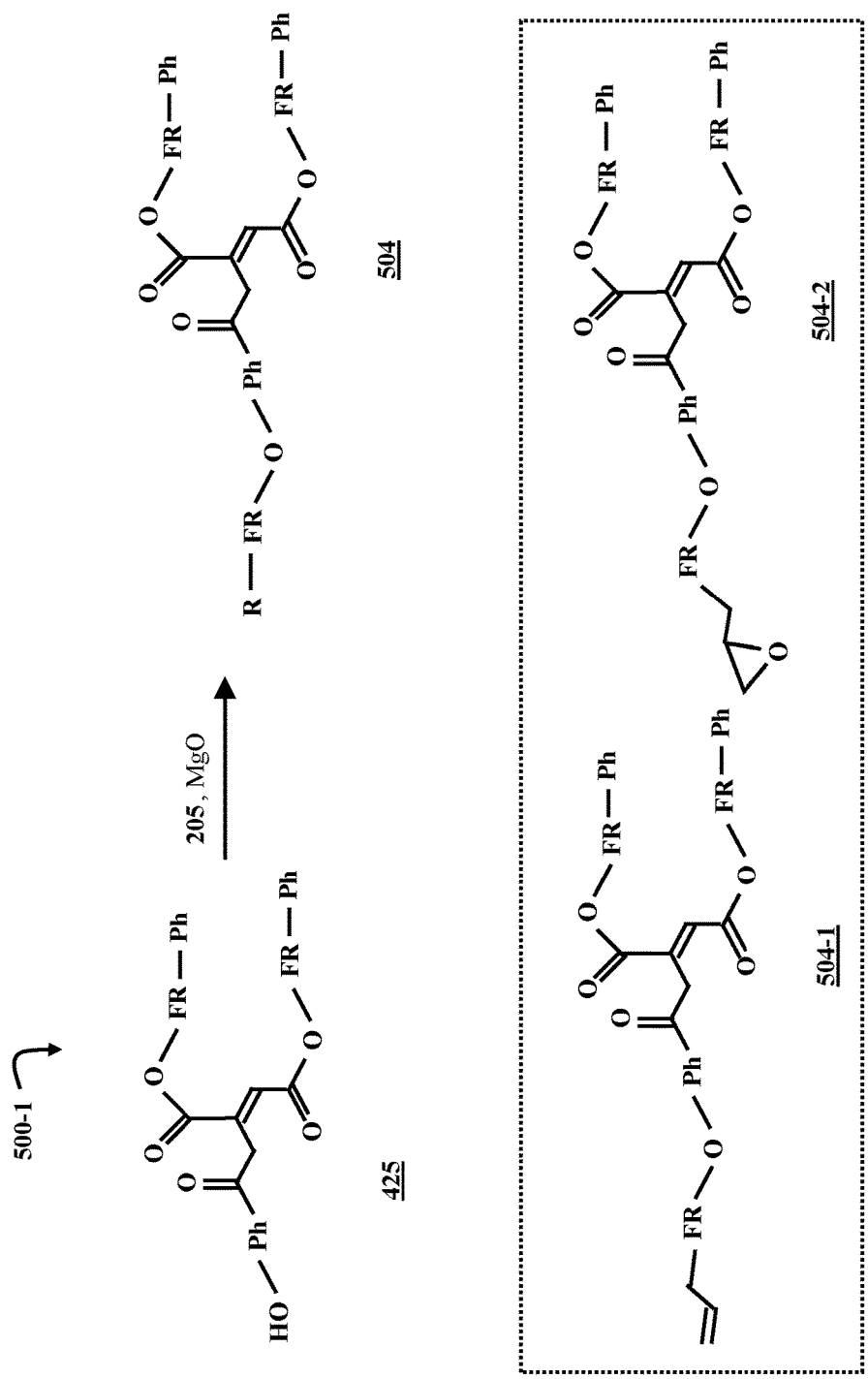
FIG. 5A is a chemical reaction diagram illustrating a process of synthesizing an allyl-functionalized and an epoxy-functionalized flame-retardant aconitic acid derivative, according to some embodiments of the present disclosure.

FIG. 5A is a chemical reaction diagram illustrating a process 500-1 of synthesizing an allyl-functionalized and an epoxy-functionalized flame-retardant aconitic acid derivative 504, according to some embodiments of the present disclosure. In this reaction, the phenol-functionalized flame-retardant aconitic acid derivative 425 is reacted with an R-functionalized phosphorus-based flame-retardant molecule 205 in the presence of magnesium oxide (MgO). The reaction between the derivative 425 and the R-functionalized phosphorus-based flame-retardant molecules 205 produces the functionalized flame-retardant aconitic acid derivative 504.

If process 500-1 is carried out with an R-functionalized phosphorus-based flame-retardant molecule 205 having an allyl R group 307, the functionalized flame-retardant aconitic acid derivative 504 will be an allyl-functionalized flame-retardant aconitic acid derivative 504-1. Likewise, if process 500-1 is carried out with an R-functionalized phosphorus-based flame-retardant molecule 205 having an epoxy R group 308, the functionalized flame-retardant aconitic acid derivative 504 will be an epoxy-functionalized flame-retardant aconitic acid derivative 504-2. If process 500-1 is carried out with the R-functionalized phosphate-based flame-retardant molecule 205-1, the functionalized flame-retardant aconitic acid derivative 504 will have a phosphoryl FR group, and, if the reaction is carried out with the R-functionalized phosphonate-based flame-retardant molecule 205-2, the functionalized flame-retardant aconitic acid derivative 504 will have a phosphonyl FR group.

Figure 5B:
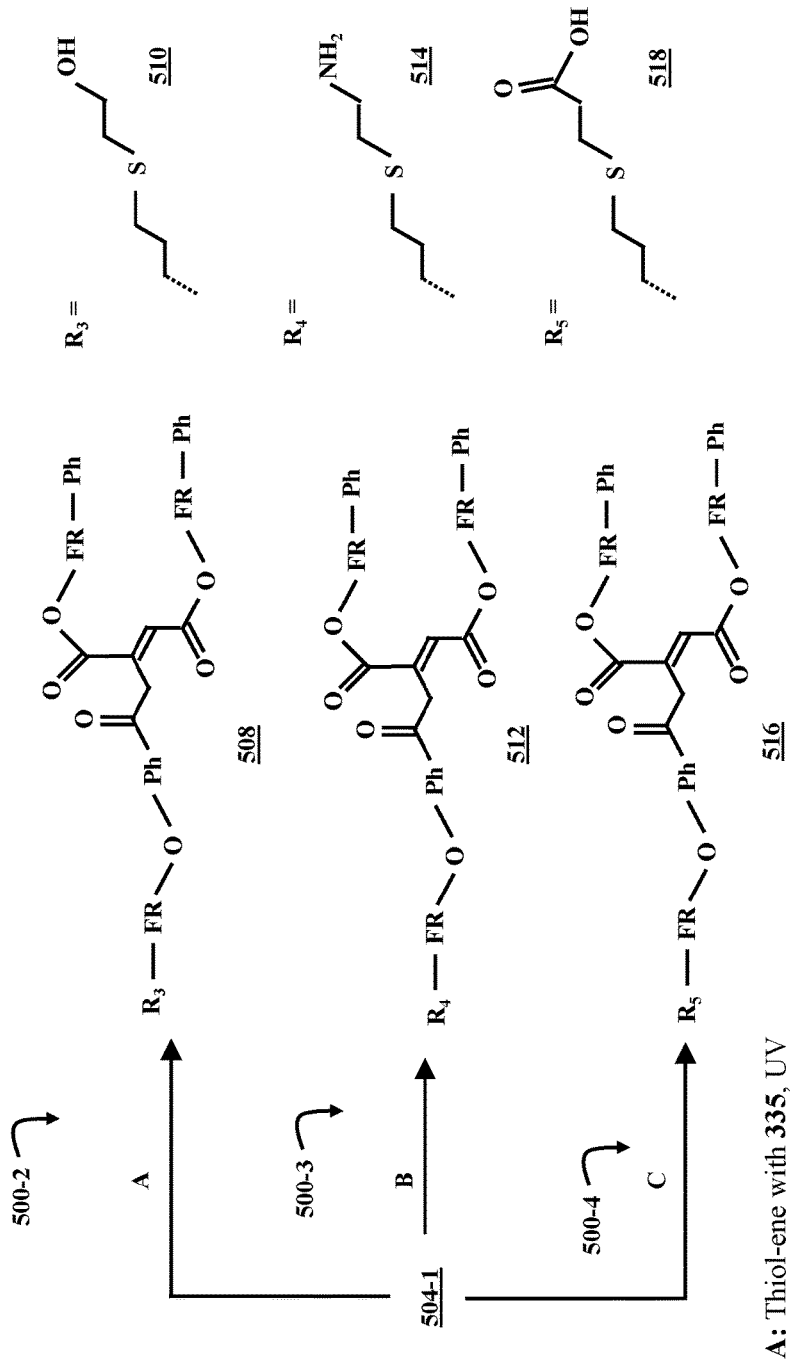
FIG. 5B is a chemical reaction diagram illustrating three processes of synthesizing thioether-linked flame-retardant aconitic acid derivatives, according to some embodiments of the present disclosure.

FIG. 5B is a chemical reaction diagram illustrating three processes 500-2, 500-3, and 500-4 of synthesizing thioether-linked flame-retardant aconitic acid derivatives, according to some embodiments of the present disclosure. Each process is a thiol-ene reaction between the allyl-functionalized flame-retardant aconitic acid derivative 504-1 and a thiol molecule. The thiol molecules used in processes 500-2, 500-3, and 500-4 are 2-mercaptoethanol 335, cysteamine HCl 340, and 3-mercaptopropionate 345, respectively. The structures of these thiol molecules are illustrated in FIG. 3C.

In process 500-2, the allyl-functionalized flame-retardant aconitic acid derivative 504-1 is reacted with 2-mercaptoethanol 335 under UV light. The resulting hydroxyl-functionalized flame-retardant aconitic acid derivative 508 has a thioether $R_3$ group 510 that corresponds to 2-mercaptoethanol 335. In process 500-3, the allyl-functionalized flame-retardant aconitic acid derivative 504-1 is reacted with cysteamine HCl 340 in a pH 9 methanol (MeOH) solution under UV light. The resulting amino-functionalized flame-retardant aconitic acid derivative 512 has a thioether $R_4$ group 514 that corresponds to cysteamine HCl 340. In process 500-4, the allyl-functionalized flame-retardant aconitic acid derivative 504-1 is reacted with 3-mercaptopropionate 345 under UV light in a methanol (MeOH) solution. The resulting carboxylic-acid functionalized flame-retardant aconitic acid derivative 516 has a thioether $R_5$ group 518 that corresponds to 3-mercaptopropionate 345.

Figure 5C:
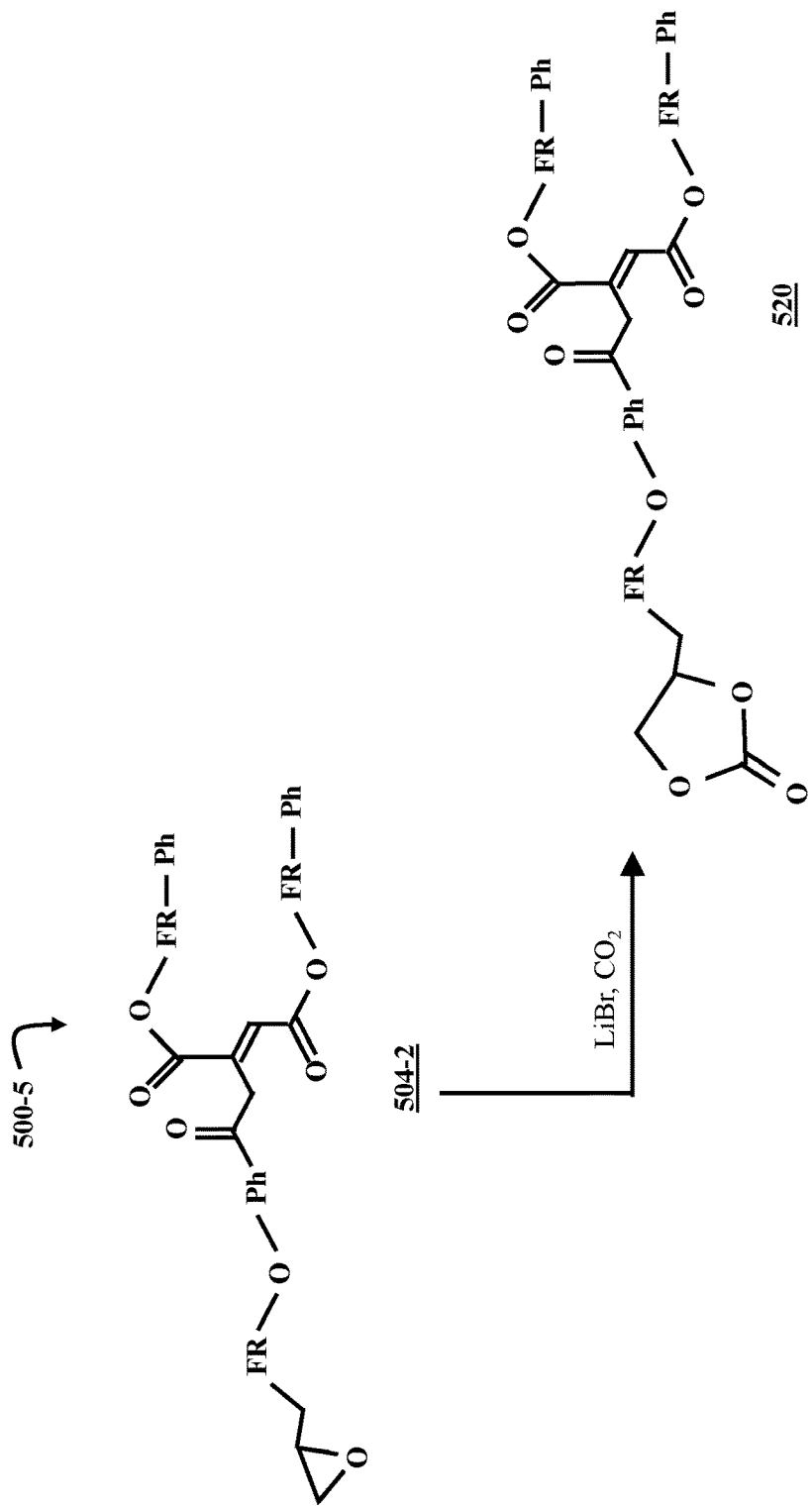
FIG. 5C is a chemical reaction diagram illustrating a process of synthesizing a propylene carbonate-functionalized flame-retardant aconitic acid derivative, according to some embodiments of the present disclosure.

FIG. 5C is a chemical reaction diagram illustrating a process 500-5 of synthesizing a propylene carbonate-functionalized flame-retardant aconitic acid derivative 520, according to some embodiments of the present disclosure. The epoxy-functionalized flame-retardant aconitic acid derivative 504-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant aconitic acid derivative 520.

Figure 5D:
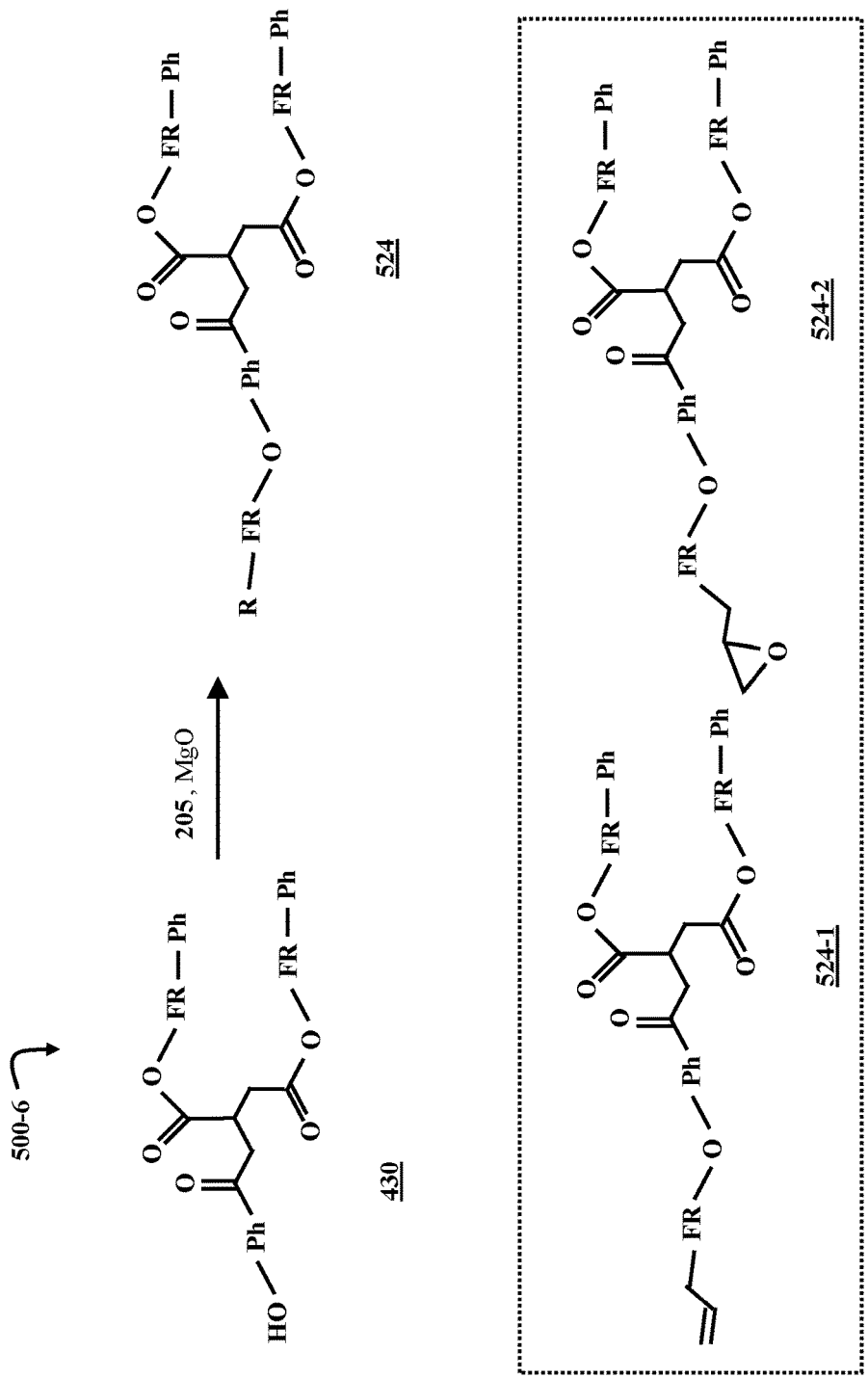
FIG. 5D is a chemical reaction diagram illustrating a process of synthesizing an allyl-functionalized and an epoxy-functionalized flame-retardant carboxysuccinic acid derivative, according to some embodiments of the present disclosure.

FIG. 5D is a chemical reaction diagram illustrating a process 500-6 of synthesizing an allyl-functionalized and an epoxy-functionalized flame-retardant carboxysuccinic acid derivative 524, according to some embodiments of the present disclosure. In this reaction, the phenol-functionalized flame-retardant carboxysuccinic acid derivative 430 is reacted with an R-functionalized phosphorus-based flame-retardant molecule 205 in the presence of magnesium oxide (MgO). The reaction between the derivative 430 and the R-functionalized phosphorus-based flame-retardant molecules 205 produces the functionalized flame-retardant carboxysuccinic acid derivative 524.

If process 500-6 is carried out with an R-functionalized phosphorus-based flame-retardant molecule 205 having an allyl R group 307, the functionalized flame-retardant carboxysuccinic acid derivative 524 will be an allyl-functionalized flame-retardant carboxysuccinic acid derivative 524-1. Likewise, if process 500-6 is carried out with an R-functionalized phosphorus-based flame-retardant molecule 205 having an epoxy R group 308, the functionalized flame-retardant carboxysuccinic acid derivative 524 will be an epoxy-functionalized flame-retardant aconitic acid derivative 524-2. If process 500-6 is carried out with the R-functionalized phosphate-based flame-retardant molecule 205-1, the functionalized flame-retardant carboxysuccinic acid derivative 524 will have a phosphoryl FR group, and, if the reaction is carried out with the R-functionalized phosphonate-based flame-retardant molecule 205-2, the functionalized flame-retardant carboxysuccinic acid derivative 524 will have a phosphonyl FR group.

Figure 5E:
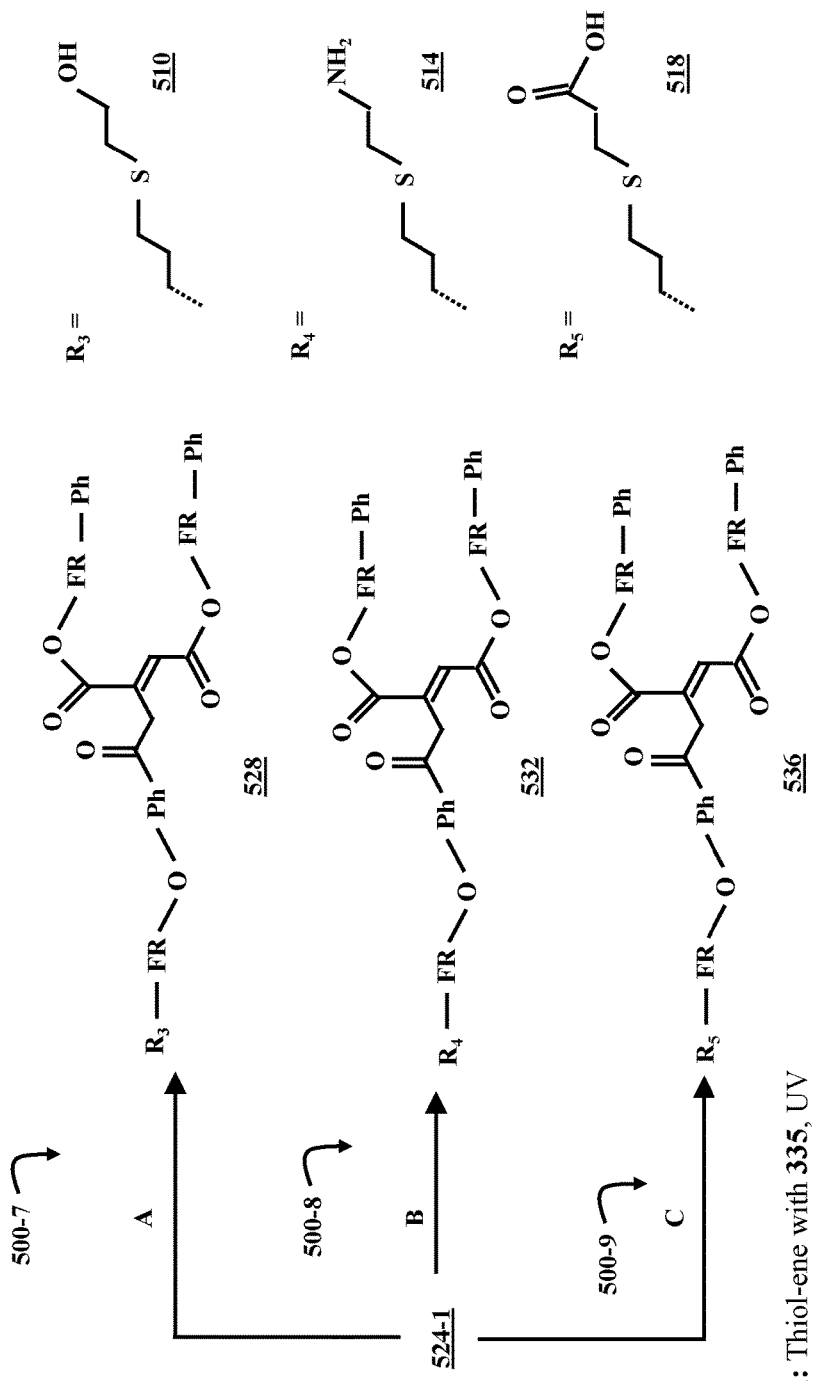
FIG. 5E is a chemical reaction diagram illustrating three processes of synthesizing thioether-linked flame-retardant carboxysuccinic acid derivatives, according to some embodiments of the present disclosure

FIG. 5E is a chemical reaction diagram illustrating three processes 500-7, 500-8, and 500-9 of synthesizing thioether-linked flame-retardant carboxysuccinic acid derivatives, according to some embodiments of the present disclosure. Each process is a thiol-ene reaction between the allyl-functionalized flame-retardant carboxysuccinic acid derivative 524-1 and a thiol molecule. The thiol molecules used in processes 500-7, 500-8, and 500-9 are 2-mercaptoethanol 335, cysteamine HCl 340, and 3-mercaptopropionate 345, respectively. The structures of these thiol molecules are illustrated in FIG. 3C.

In process 500-7, the allyl-functionalized flame-retardant carboxysuccinic acid derivative 524-1 is reacted with 2-mercaptoethanol 335 under UV light. The resulting hydroxyl-functionalized flame-retardant butenetriol derivative 528 has a thioether $R_3$ group 510 that corresponds to 2-mercaptoethanol 335. In process 500-8, the allyl-functionalized flame-retardant carboxysuccinic acid derivative 524-1 is reacted with cysteamine HCl 340 in a pH 9 methanol (MeOH) solution under UV light. The resulting amino-functionalized flame-retardant carboxysuccinic acid derivative 532 has a thioether $R_4$ group 514 that corresponds to cysteamine HCl 340. In process 500-9, the allyl-functionalized flame-retardant carboxysuccinic acid derivative 524-1 is reacted with 3-mercaptopropionate 345 under UV light in a methanol (MeOH) solution. The resulting carboxylic-acid functionalized flame-retardant carboxysuccinic acid derivative 536 has a thioether $R_5$ group 518 that corresponds to 3-mercaptopropionate 345.

Figure 5F:
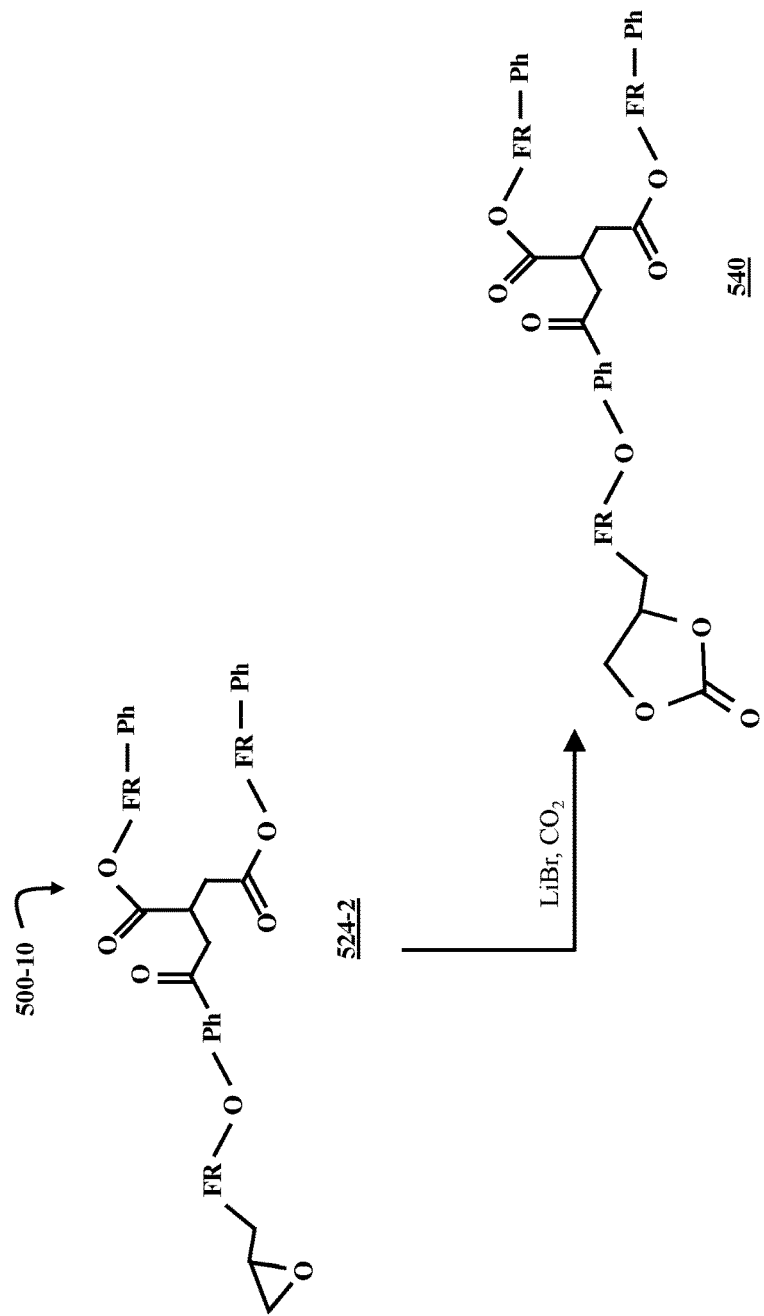
FIG. 5F is a chemical reaction diagram illustrating a process of synthesizing a propylene carbonate-functionalized flame-retardant carboxysuccinic acid derivative, according to some embodiments of the present disclosure.

FIG. 5F is a chemical reaction diagram illustrating a process 500-10 of synthesizing a propylene carbonate-functionalized flame-retardant carboxysuccinic acid derivative 540, according to some embodiments of the present disclosure. The epoxy-functionalized flame-retardant carboxysuccinic acid derivative 524-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant carboxysuccinic acid derivative 540.

Figure 5G:
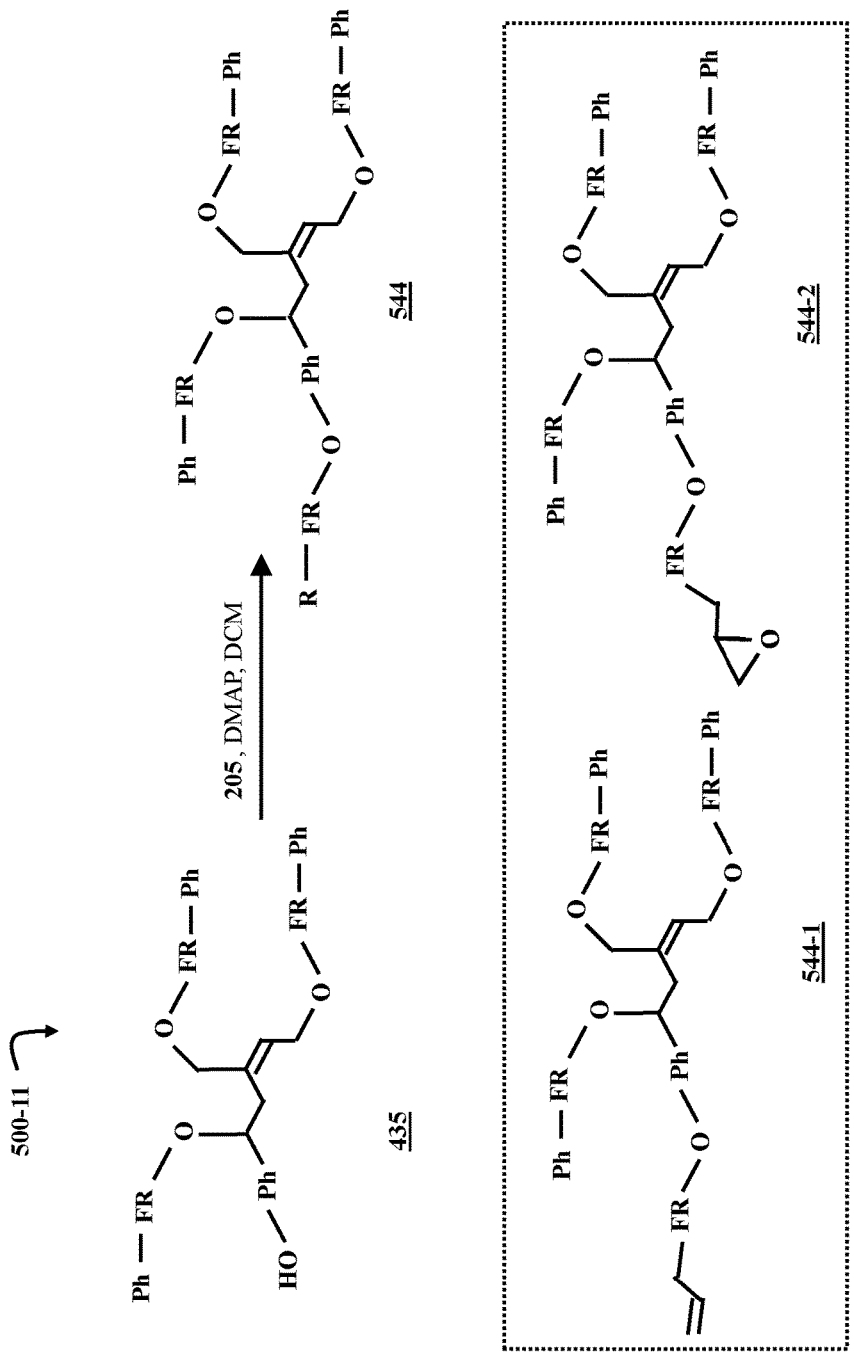
FIG. 5G is a chemical reaction diagram illustrating a process of synthesizing an allyl-functionalized and an epoxy-functionalized flame-retardant butenetriol derivative, according to some embodiments of the present disclosure.

FIG. 5G is a chemical reaction diagram illustrating a process 500-11 of synthesizing an allyl-functionalized and an epoxy-functionalized flame-retardant butenetriol derivative 544, according to some embodiments of the present disclosure. In this reaction, the phenol-functionalized flame-retardant butenetriol derivative 435 is reacted with an R-functionalized phosphorus-based flame-retardant molecule 205 and catalytic dimethylaminopyridine (DMAP) in a dichloromethane (DCM) solution. The reaction between the derivative 435 and the R-functionalized phosphorus-based flame-retardant molecules 205 produces the functionalized flame-retardant butenetriol derivative 544.

If process 500-11 is carried out with an R-functionalized phosphorus-based flame-retardant molecule 205 having an allyl R group 307, the functionalized flame-retardant butenetriol derivative 544 will be an allyl-functionalized flame-retardant butenetriol derivative 544-1. Likewise, if process 500-11 is carried out with an R-functionalized phosphorus-based flame-retardant molecule 205 having an epoxy R group 308, the functionalized flame-retardant butenetriol derivative 544 will be an epoxy-functionalized flame-retardant butenetriol derivative 544-2. If process 500-11 is carried out with the R-functionalized phosphate-based flame-retardant molecule 205-1, the functionalized flame-retardant butenetriol derivative 544 will have a phosphoryl FR group, and, if the reaction is carried out with the R-functionalized phosphonate-based flame-retardant molecule 205-2, the functionalized flame-retardant butenetriol derivative 544 will have a phosphonyl FR group.

Figure 5H:
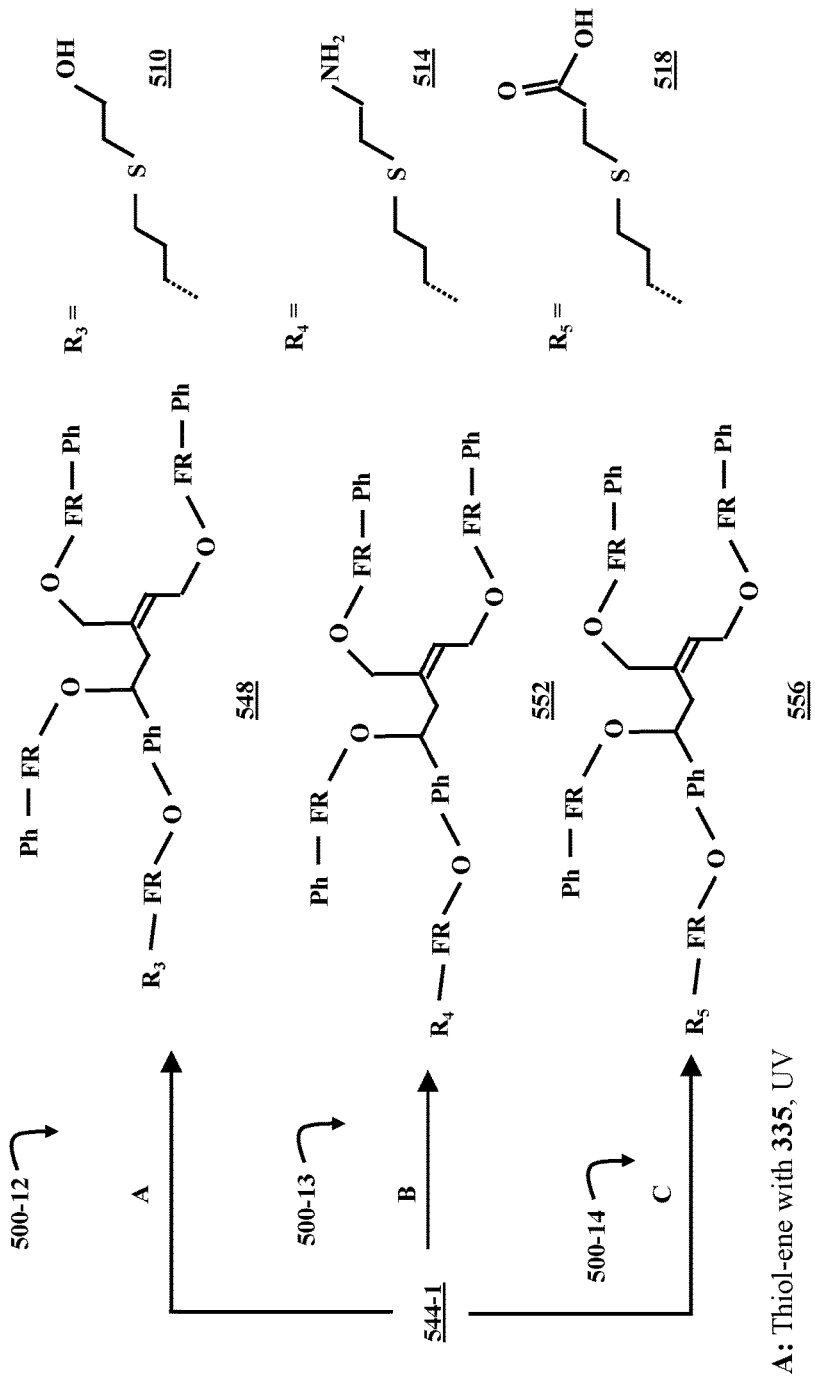
FIG. 5H is a chemical reaction diagram illustrating three processes of synthesizing thioether-linked flame-retardant butenetriol derivatives, according to some embodiments of the present disclosure.

FIG. 5H is a chemical reaction diagram illustrating three processes 500-12, 500-13, and 500-14 of synthesizing thioether-linked flame-retardant butenetriol derivatives, according to some embodiments of the present disclosure. Each process is a thiol-ene reaction between the allyl-functionalized flame-retardant butenetriol derivative 544-1 and a thiol molecule. The thiol molecules used in processes 500-12, 500-13, and 500-14 are 2-mercaptoethanol 335, cysteamine HCl 340, and 3-mercaptopropionate 345, respectively. The structures of these thiol molecules are illustrated in FIG. 3C.

In process 500-12, the allyl-functionalized flame-retardant butenetriol derivative 544-1 is reacted with 2-mercaptoethanol 335 under UV light. The resulting hydroxyl-functionalized flame-retardant butenetriol derivative 548 has a thioether $R_3$ group 510 that corresponds to 2-mercaptoethanol 335. In process 500-13, the allyl-functionalized flame-retardant butenetriol derivative 544-1 is reacted with cysteamine HCl 340 in a pH 9 methanol (MeOH) solution under UV light. The resulting amino-functionalized flame-retardant butenetriol derivative 552 has a thioether $R_4$ group 514 that corresponds to cysteamine HCl 340. In process 500-14, the allyl-functionalized flame-retardant butenetriol derivative 544-1 is reacted with 3-mercaptopropionate 345 under UV light in a methanol (MeOH) solution. The resulting carboxylic-acid functionalized flame-retardant butenetriol derivative 556 has a thioether $R_5$ group 518 that corresponds to 3-mercaptopropionate 345.

Figure 5I:
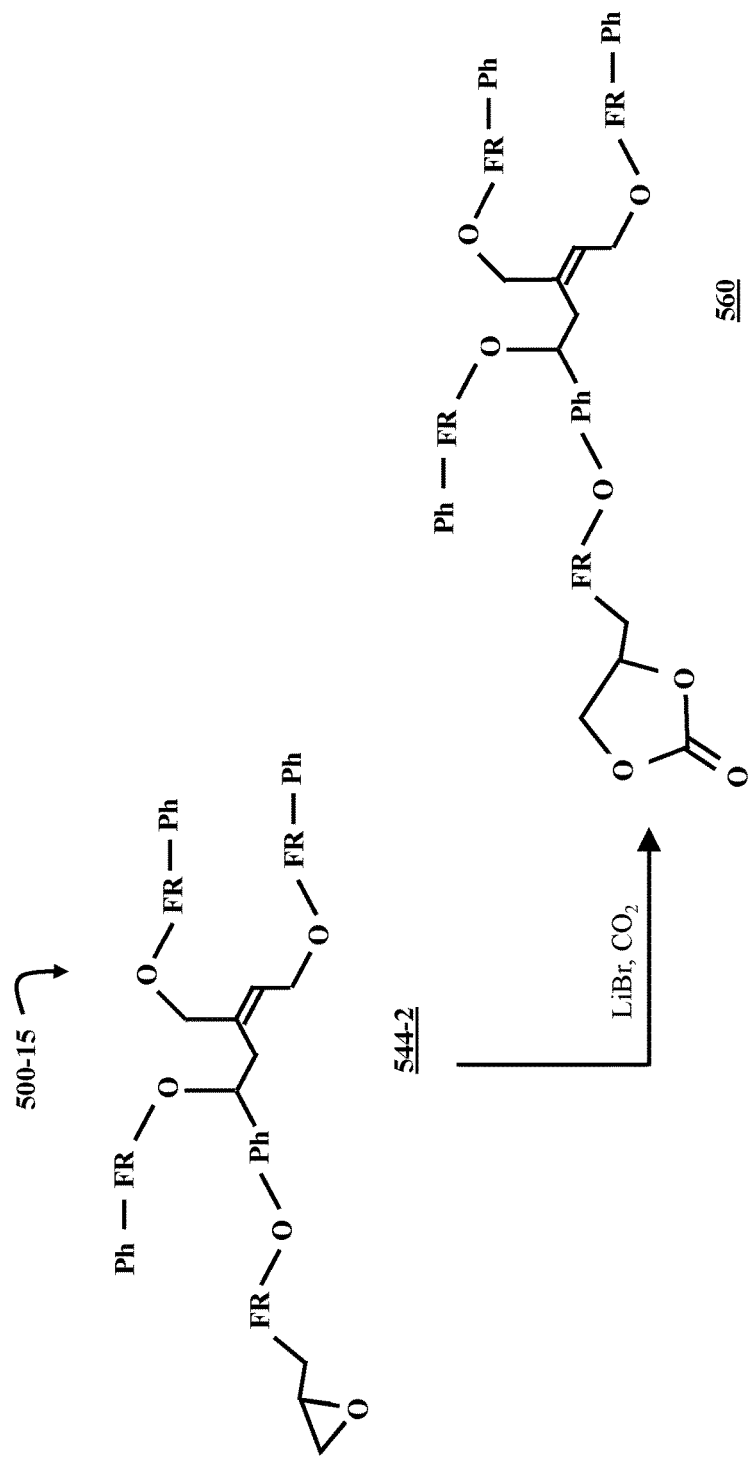
FIG. 5I is a chemical reaction diagram illustrating a process of synthesizing a propylene carbonate-functionalized flame-retardant butenetriol derivative, according to some embodiments of the present disclosure.

FIG. 5I is a chemical reaction diagram illustrating a process 500-15 of synthesizing a propylene carbonate-functionalized flame-retardant butenetriol derivative 560, according to some embodiments of the present disclosure. The epoxy-functionalized flame-retardant butenetriol derivative 544-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant butenetriol derivative 560.

Figure 5J:
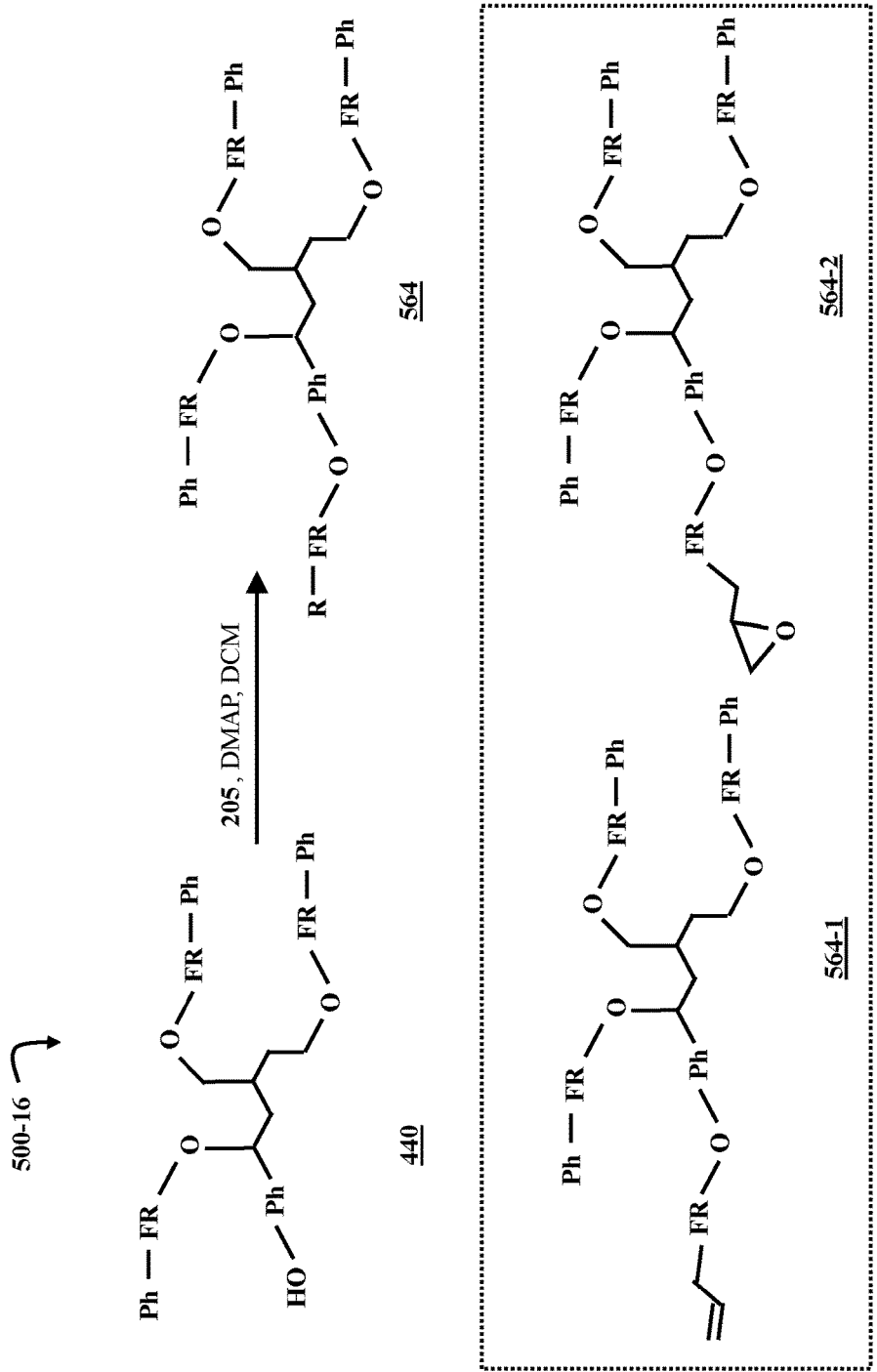
FIG. 5J is a chemical reaction diagram illustrating a process of synthesizing an allyl-functionalized and an epoxy-functionalized flame-retardant butanetriol derivative, according to some embodiments of the present disclosure.

FIG. 5J is a chemical reaction diagram illustrating a process 500-16 of synthesizing an allyl-functionalized and an epoxy-functionalized flame-retardant butanetriol derivative 564, according to some embodiments of the present disclosure. In this reaction, the phenol-functionalized butanetriol derivative 445 is reacted with an R-functionalized phosphorus-based flame-retardant molecule 205 and catalytic dimethylaminopyridine (DMAP) in a dichloromethane (DCM) solution. The reaction between the derivative 445 and the R-functionalized phosphorus-based flame-retardant molecules 205 produces the functionalized flame-retardant butanetriol derivative 564.

If process 500-16 is carried out with an R-functionalized phosphorus-based flame-retardant molecule 205 having an allyl R group 307, the functionalized flame-retardant butanetriol derivative 564 will be an allyl-functionalized flame-retardant butanetriol derivative 564-1. Likewise, if process 500-16 is carried out with an R-functionalized phosphorus-based flame-retardant molecule 205 having an epoxy R group 308, the functionalized flame-retardant butanetriol derivative 564 will be an epoxy-functionalized flame-retardant butanetriol derivative 564-2. If process 500-16 is carried out with the R-functionalized phosphate-based flame-retardant molecule 205-1, the functionalized flame-retardant butanetriol derivative 564 will have a phosphoryl FR group, and, if the reaction is carried out with the R-functionalized phosphonate-based flame-retardant molecule 205-2, the functionalized flame-retardant butanetriol derivative 564 will have a phosphonyl FR group.

Figure 5K:
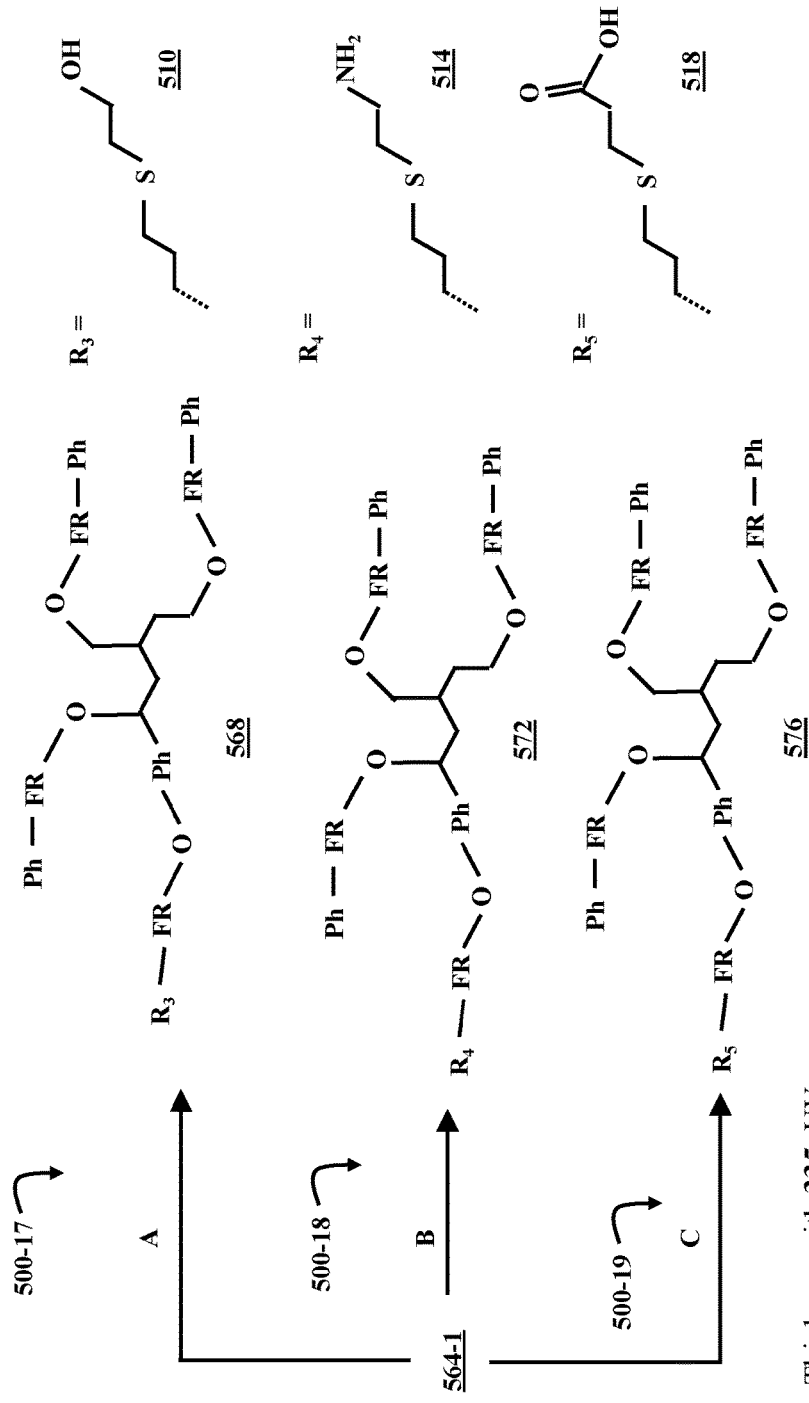
FIG. 5K is a chemical reaction diagram illustrating three processes of synthesizing thioether-linked flame-retardant butanetriol derivatives, according to some embodiments of the present disclosure.

FIG. 5K is a chemical reaction diagram illustrating three processes 500-17, 500-18, and 500-19 of synthesizing thioether-linked flame-retardant butanetriol derivatives, according to some embodiments of the present disclosure. Each process is a thiol-ene reaction between the allyl-functionalized flame-retardant butanetriol derivative 564-1 and a thiol molecule. The thiol molecules used in processes 500-17, 500-18, and 500-19 are 2-mercaptoethanol 335, cysteamine HCl 340, and 3-mercaptopropionate 345, respectively. The structures of these thiol molecules are illustrated in FIG. 3C.

In process 500-17, the allyl-functionalized flame-retardant butanetriol derivative 564-1 is reacted with 2-mercaptoethanol 335 under UV light. The resulting hydroxyl-functionalized flame-retardant butanetriol derivative 568 has a thioether $R_3$ group 510 that corresponds to 2-mercaptoethanol 335. In process 500-18, the allyl-functionalized flame-retardant butanetriol derivative 564-1 is reacted with cysteamine HCl 340 in a pH 9 methanol (MeOH) solution under UV light. The resulting amino-functionalized flame-retardant butanetriol derivative 572 has a thioether $R_4$ group 514 that corresponds to cysteamine HCl 340. In process 500-19, the allyl-functionalized flame-retardant butanetriol derivative 564-1 is reacted with 3-mercaptopropionate 345 under UV light in a methanol (MeOH) solution. The resulting carboxylic-acid functionalized flame-retardant butanetriol derivative 576 has a thioether $R_5$ group 518 that corresponds to 3-mercaptopropionate 345.

Figure 5L:
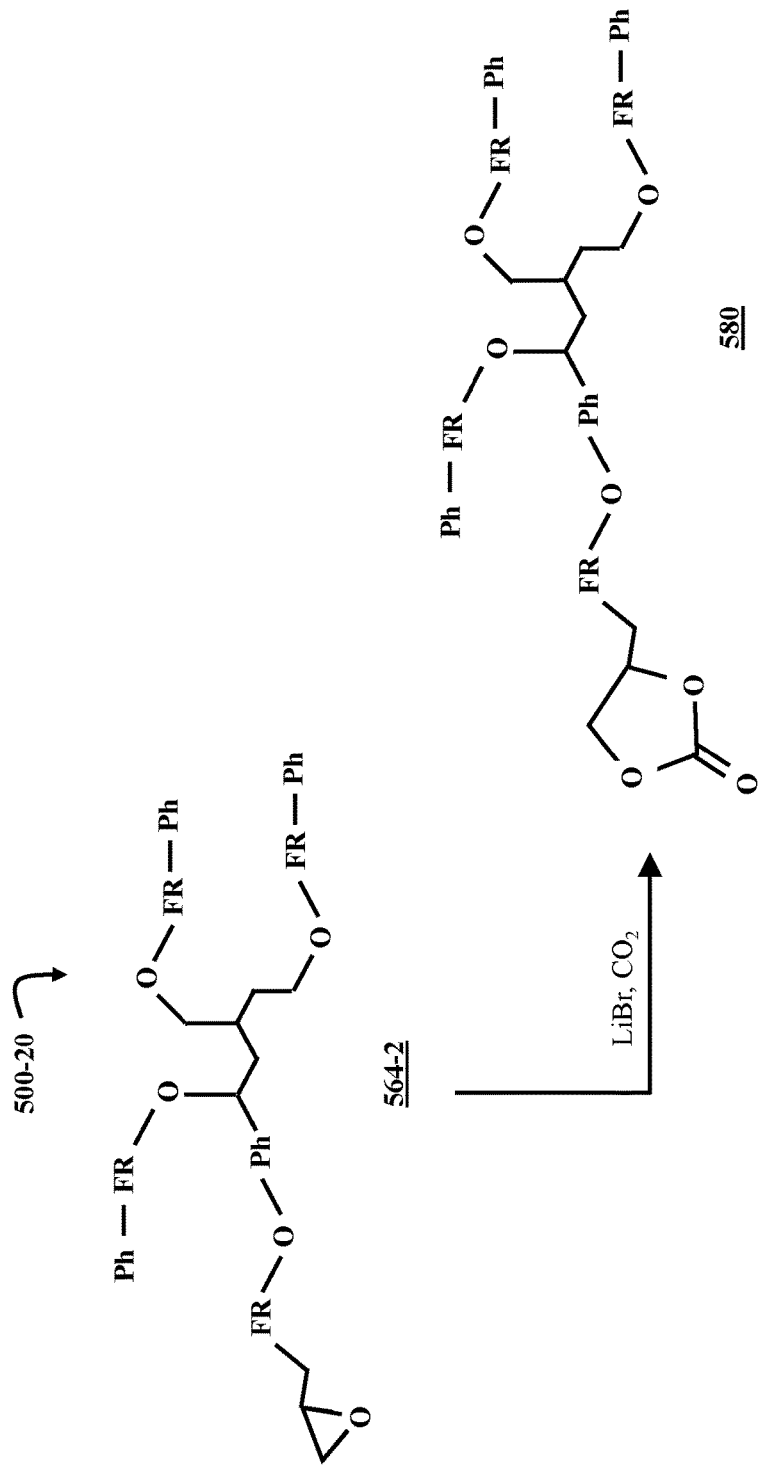
FIG. 5L is a chemical reaction diagram illustrating a process of synthesizing a propylene carbonate-functionalized flame-retardant butanetriol derivative, according to some embodiments of the present disclosure.

FIG. 5L is a chemical reaction diagram illustrating a process 500-20 of synthesizing a propylene carbonate-functionalized flame-retardant butanetriol derivative 580, according to some embodiments of the present disclosure. The epoxy-functionalized flame-retardant butanetriol derivative 564-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant butanetriol derivative 580.

In some embodiments, the processes 500-1, 500-6, 500-11, and 500-16 of forming functionalized flame-retardant aconitic acid-derived molecules are carried out with a mixture of both the R-functionalized phosphate-based 205-1 and the phosphonate-based 205-2 flame retardant molecules. These processes are discussed in greater detail with regard to FIGS. 5A, 5D, 5G, and 5J, respectively. Reacting a phenol-functionalized derivative with a mixture of the R-functionalized phosphate—205-1 and phosphonate-based 205-2 flame retardant molecules can result in flame-retardant aconitic acid-derived molecules with both phosphoryl and phosphonyl FR groups. However, in some instances, adding a mixture of R-functionalized phosphate—205-1 and phosphonate-based 205-2 flame retardant molecules can result in the production of flame-retardant aconitic acid-derived molecules with all phosphoryl or all phosphonyl FR groups. Additionally, adding both R-functionalized flame-retardant molecules 205-1 and 205-2 to the reaction can yield a mixture of products that includes some combination of flame-retardant aconitic acid-derived molecules with either all phosphoryl or all phosphonyl FR groups and flame-retardant aconitic acid-derived molecules with both phosphoryl and phosphonyl FR groups.

The functionalized flame-retardant aconitic acid-derived molecules disclosed herein bind to polymers via their R functional groups, imparting flame-retardant properties to the polymers. The functionalized flame-retardant aconitic acid-derived molecules can also be bound to non-polymeric resins, varnishes, and adhesives. The non-polymeric resins, varnishes, and adhesives are also made flame-retardant by the attachment of the bound functionalized flame-retardant aconitic acid-derived molecules. The flame-retardant materials can be used in a number of devices.

One example of a polymer that can be made flame-retardant by the addition of functionalized flame-retardant aconitic acid-derived molecules is polycarbonate-acrylonitrile butadiene styrene (PC-ABS), a plastic that is often used in electronics hardware. Functionalized flame-retardant aconitic acid-derived molecules can also be incorporated into polyurethane. Polyurethane is a versatile polymer used in applications that can include acoustic dampening, cushioning, plastics, synthetic fibers, insulation, adhesives, etc. The functionalized flame-retardant aconitic acid-derived molecules can also be added to adhesives such as bio-adhesives, elastomers, thermoplastics, emulsions, thermosets, etc. Further, materials containing the functionalized flame-retardant aconitic acid-derived molecules can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating functionalized flame-retardant aconitic acid-derived molecules. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Functionalized flame-retardant aconitic acid-derived molecules can be bound to the polymers in the PCB resin in order to prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. In some instances, reactions that involve multiple steps can be carried out sequentially, and, in other instances, they can be carried out in one pot. Further, in some embodiments, processes can be added or omitted while still remaining within the scope of the disclosure, as will be understood by a person of ordinary skill in the art.

What is claimed is:

1. A functionalized flame-retardant aconitic acid-derived molecule comprising:

at least one phosphorus-based moiety with a formula selected from a group consisting of:

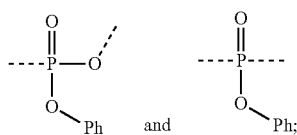

and a functional group, wherein the functional group binds to a polymer.

2. The functionalized flame-retardant aconitic acid-derived molecule of claim 1, wherein the functionalized flame-retardant aconitic acid-derived molecule is selected from a group consisting of molecules with formulas of:

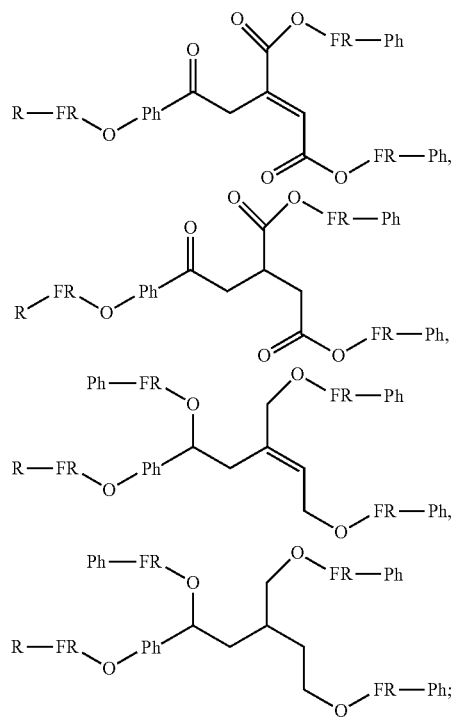

and
wherein FR is the at least one phosphorus-based moiety; and
wherein R is selected from a group consisting of an allyl functional group, an epoxy functional group, a propylene carbonate substituent, and a functionalized thioether substituent.

3. The functionalized flame-retardant aconitic acid-derived molecule of claim 2, wherein the functionalized thioether substituent is selected from a group consisting of a hydroxyl-functionalized thioether substituent, an amino-functionalized thioether substituent, and a carboxylic acid-functionalized thioether substituent.

4. The functionalized flame-retardant aconitic acid-derived molecule of claim 1, wherein the functionalized flame-retardant aconitic acid-derived molecule is synthesized from aconitic acid obtained from a bio-based source.

5. The functionalized flame-retardant aconitic acid-derived molecule of claim 4, wherein the bio-based source is citric acid.

6. A process of forming a flame-retardant polymer, comprising:

forming a phosphorus-based flame-retardant molecule selected from a group consisting of phosphorus-based molecules with formulas of:

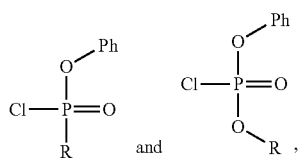

wherein R is selected from a group consisting of an epoxy functional group and an allyl functional group;
forming an aconitic acid derivative;

chemically reacting the aconitic acid derivative with the phosphorus-based flame-retardant molecule to form a functionalized flame-retardant aconitic acid-derived molecule; and binding the functionalized flame-retardant aconitic acid-derived molecule to a polymer to form the flame-retardant polymer.

7. The process of claim 6, wherein the aconitic acid derivative is synthesized from aconitic acid that has been obtained from a bio-based source.

8. The process of claim 6, wherein the aconitic acid derivative is selected from a group consisting of:

a phenol-functionalized aconitic acid derivative with a formula of:

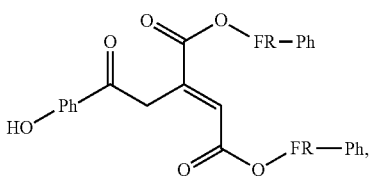

a phenol-functionalized carboxysuccinic acid derivative with a formula of:

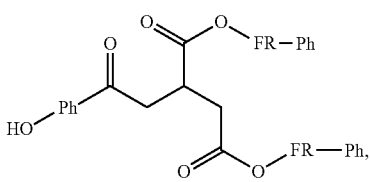

a phenol-functionalized butenetriol derivative with a formula of:

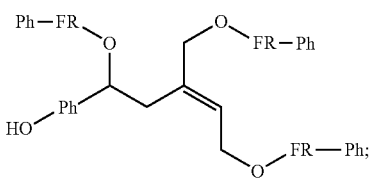

and a phenol-functionalized butanetriol derivative with a formula of:

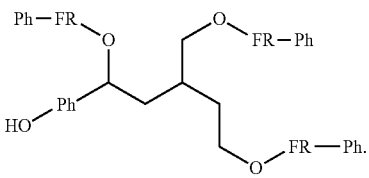

9. The process of claim 6, further comprising chemically reacting the functionalized flame-retardant aconitic acid-derived molecule with a thiol molecule to form a thioether-linked flame-retardant aconitic acid-derived molecule.

10. The process of claim 9, wherein the thiol molecule is selected from a group consisting of 2-mercaptoethanol, cysteamine hydrochloride, and 3-mercaptopropionate.

11. The process of claim 6, further comprising chemically reacting the functionalized flame-retardant aconitic acid-derived molecule with lithium bromide and carbon dioxide to form a propylene carbonate-functionalized flame-retardant aconitic acid-derived molecule.

12. An article of manufacture, comprising:

a material containing a functionalized flame-retardant aconitic acid-derived molecule, the molecule comprising:

at least one phosphorus-based moiety with a formula selected from a group of formulas consisting of:

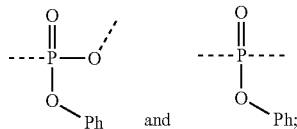

and at least one substituent bound to the at least one phosphorus-based moiety.

13. The article of manufacture of claim 12, wherein the material is a resin.

14. The article of manufacture of claim 12, wherein the material is a plastic.

15. The article of manufacture of claim 12, wherein the material is an adhesive.

16. The article of manufacture of claim 12, wherein the material is a polymer selected from a group consisting of polyurethane, an epoxy, a polyhydroxyurethane, a polycarbonate, a polyester, a polyacrylate, a polyimide, a polyamide, a polyurea, and a poly(vinyl-ester).

17. The article of manufacture of claim 12, further comprising an electronic component.

* * * * *